United States Patent
Beaudoin et al.

(10) Patent No.: US 10,365,209 B1
(45) Date of Patent: Jul. 30, 2019

(54) APPARATUS AND METHOD FOR PERFORMING DISSOLVED GAS ANALYSIS ON A PIECE OF ELECTRICAL EQUIPMENT USING RESONANT PHOTO-ACOUSTIC SPECTROSCOPY AND USE THEREOF

(71) Applicant: MORGAN SCHAFFER LTD., LaSalle (CA)

(72) Inventors: Alexandre Beaudoin, Montréal (CA); Stephan Brauer, Montréal (CA); Nicholas Lebel-Buchanan, Montréal (CA); Andrew MacGillivray, Montréal (CA); Niculae Mincu, Pointe-Claire (CA); Samuel René de Cotret, Montréal (CA); Stefan Voinea, Brossard (CA)

(73) Assignee: Morgan Schaffer Ltd., Quebec (CA)

( * ) Notice: Subject to any disclaimer, the term of this patent is extended or adjusted under 35 U.S.C. 154(b) by 63 days.

(21) Appl. No.: 15/813,747

(22) Filed: Nov. 15, 2017

(51) Int. Cl.
*G01N 21/17* (2006.01)
*G01N 21/25* (2006.01)
(Continued)

(52) U.S. Cl.
CPC ......... *G01N 21/1702* (2013.01); *G01N 21/25* (2013.01); *G01N 33/004* (2013.01); *G01N 33/26* (2013.01); *G01N 2021/1704* (2013.01)

(58) Field of Classification Search
CPC ....... G01N 21/1702; G01N 2021/1704; G01N 2021/0193; G01N 21/25; G01N 33/004; G01N 33/0036; G01N 33/26
(Continued)

(56) References Cited

U.S. PATENT DOCUMENTS 4,163,382 A * 8/1979 Amer ................. G01N 21/1702
250/351
6,391,096 B1 5/2002 Waters et al.
(Continued)

FOREIGN PATENT DOCUMENTS

WO WO 2008/074442 6/2008
WO WO 2016/179693 11/2016

OTHER PUBLICATIONS

Miklos et al. "Application of acoustic resonators in photacoustic trace gas analysis and metrology," Review of Scientific Instruments, Apr. 2001, vol. 72, No. 4, pp. 1937-1955.
(Continued)

*Primary Examiner* — Robert R Raevis
(74) *Attorney, Agent, or Firm* — Sheridan Ross P.C.

(57) ABSTRACT

An apparatus is described for performing dissolved gas analysis on electrical equipment having components immersed in electrical insulating liquid. The apparatus comprises an analyzer including a photo-acoustic spectroscopy (PAS) measurement system for performing gas analysis on a gas sample wherein the PAS measurement system has an elongated channel including a resonant cavity and an electromagnetic energy source. The resonant cavity includes a first portion and a second portion configured for containing at least part of the gas sample, wherein the first portion defines an optical pathway configured for propagation of electromagnetic energy from the electromagnetic energy source. The resonant cavity includes an element configured for obstructing the propagation of the electromagnetic energy through to the second portion of the resonant cavity. The PAS measurement system is configured to excite a portion of the gas sample in the optical pathway to produce a photo-acoustic signal, which may then be processed to derive information associated with dissolved gas concentrations in the electrical insulating liquid. In some implemen-
(Continued)

tations, a pressure regulating element may be used to regulate the pressure in a gas extraction cell so that the pressure lies within a target pressure range. In some implementations, the electromagnetic energy source may be configured to produce a periodically pulsed beam of electromagnetic radiation having a chopping frequency greater than or equal to 150 Hz. One or more damper elements may be used for reducing vibrational interferences with some of the measurement equipment.

25 Claims, 13 Drawing Sheets

(51) Int. Cl.
*G01N 33/00* (2006.01)
*G01N 33/26* (2006.01)

(58) Field of Classification Search
USPC ..................... 73/19.01, 19.03, 24.01, 24.02
See application file for complete search history.

(56) References Cited

U.S. PATENT DOCUMENTS

| | | | |
|---|---|---|---|
| 7,263,871 B2 | 9/2007 | Selker et al. | |
| 7,398,672 B2 | 7/2008 | Riddle | |
| 7,765,871 B2 | 8/2010 | Riddle | |
| 8,347,687 B2 | 1/2013 | Cunningham | |
| 2014/0026639 A1* | 1/2014 | Wang | G01N 21/3504 73/24.02 |
| 2014/0165704 A1* | 6/2014 | Maity | G01N 25/005 73/25.01 |
| 2015/0059434 A1 | 3/2015 | Maity et al. | |
| 2015/0059435 A1 | 3/2015 | Choudhury et al. | |
| 2016/0282313 A1* | 9/2016 | Robinson | G01N 29/2418 |
| 2016/0290896 A1* | 10/2016 | Calvert | G01N 33/2841 |
| 2018/0059087 A1* | 3/2018 | Robinson | F15D 1/02 |
| 2018/0136166 A1* | 5/2018 | Voinea | G01N 29/036 |

OTHER PUBLICATIONS

Skelly "The Transition to Next-Generation Online DGA Monitoring Technologies Utilizing Photo-Acoustic Spectroscopy," General Electric Company, 2013, Part 1 of 2 part series, 8 pages.

International Search Report and Written Opinion for International (PCT) Patent Application No. PCT/CA2016/050511, dated Jul. 22, 2016, 7pages.

Official Action for U.S. Appl. No. 15/572,633, dated Mar. 11, 2019, 6 pages Restriction Requirement.

\* cited by examiner

APPARATUS AND METHOD FOR PERFORMING DISSOLVED GAS ANALYSIS ON A PIECE OF ELECTRICAL EQUIPMENT USING RESONANT PHOTO-ACOUSTIC SPECTROSCOPY AND USE THEREOF

TECHNICAL FIELD

This disclosure generally relates to the field of dissolved gas analysis apparatuses using resonant photo-acoustic spectroscopy and, more specifically, in the context of detecting/monitoring faults in liquid-insulated electrical equipment.

BACKGROUND

Electrical insulating liquid (such as for example mineral oil) is commonly used in equipment that serves in the generating, transmitting, and distributing of electrical power. Such equipment generally includes transformers (sometimes called oil-immersed transformers), tap-changers and circuit breakers. In such equipment, the liquid acts as both heat dissipation and electrical insulating medium. When a fault occurs in such electrical equipment, fault gases may evolve in the insulating liquid.

The gases that are typically associated with specific fault types in such equipment are Hydrogen ($H_2$), Carbon Dioxide ($CO_2$), Carbon Monoxide (CO), Ethane ($C_2H_6$), Methane ($CH_4$), Ethylene ($C_2H_4$) and Acetylene ($C_2H_2$). Analysis of one or more of such fault gases may be used to provide a diagnosis of the health of electrical equipment.

In this regard, various practical Dissolved Gas Analysis (DGA) applications have been previously suggested for detecting such fault gases in equipment that serves in the generating, transmitting and distributing of electrical power.

For example, U.S. Pat. No. 6,391,096 to Waters describes an apparatus for performing dissolved gas analysis on electrical insulating oil which makes use of a gas chromatograph to analyze the fault gases. The apparatus includes a tubular membrane extractor column for extracting the fault gases from the oil, where the column includes a plurality of composite hollow fiber tubes coated with a thin layer of a non-porous gas permeable polymer, making each tube gas permeable, but not dielectric fluid permeable. Diffusion of the fault gases occur through the fiber tubes until equilibrium exists on both sides of the phase barrier. The time required to reach equilibrium or near equilibrium conditions depends upon factors such as pressure and temperature, the size of the diffusing molecules and the permeation properties of the media, as well as the flow rate of the oil carrying the gases for equilibrium.

U.S. Pat. No. 8,347,687 to Cunningham describes an apparatus for performing dissolved gas analysis on electrical insulating oil which makes use of photo-acoustic spectroscopy (PAS) to analyze the fault gases. The apparatus includes a gas extraction module in which the fault gases are released from the oil by means of an agitator into a head space of the module. After a period of agitation, head space equilibrium is achieved, and the gases are pumped into an analysis cell where measurements of the head space gases are performed with a PAS module. The apparatus conveniently includes a fluid conduit configuration which enables the measure of oil samples from different sources relatively easily while minimizing or avoiding cross contamination.

A deficiency associated with many commonly used apparatuses used for performing dissolved gas analysis on electrical insulating liquid (such as for example electrical insulating oil) is that they frequently use infra-red absorption methods that require relatively large sample gas volumes to be able to detect the minimal concentrations of fault gases that are relevant for detecting emerging faults in liquid-insulated electrical equipment. For example, such minimal concentrations may represent gas levels as low as 1 ppm in the case of acetylene. The requirement for relatively large sample gas volumes, however, increases manufacturing costs of other systems in the apparatus, including those required to maintain the liquid/gas samples within a specific operational temperature range to ensure measurement accuracy and reproducibility. In addition, the relatively large sample gas volumes required often lead to increases in the period of time required to extract the fault gases from each sample (i.e., the time required to reach equilibrium), which negatively impacts the time-resolution and accuracy of dissolved-gas concentration measurements of many conventional DGA apparatuses.

Against the background described above, it is clear that there remains a need in the industry to provide improved dissolved gas analysis apparatuses and methods that alleviate at least in part the deficiencies of the existing apparatuses and methods.

SUMMARY

This Summary is provided to introduce a selection of concepts in a simplified form that are further described below in the Detailed Description. This Summary is not intended to identify key aspects or essential aspects of the claimed subject matter.

As embodied and broadly described herein, the present disclosure relates to an apparatus for performing dissolved gas analysis on a piece of electrical equipment having components immersed in electrical insulating liquid, the apparatus comprising:

a. a liquid inlet and a liquid outlet connectable to the piece of electrical equipment for allowing electrical insulating liquid to circulate between the piece of electrical equipment and the apparatus through a liquid circulation path;

b. a gas extraction cell in communication with the liquid circulation path, said gas extraction cell being configured for extracting a gas sample from the electrical insulating liquid;

c. an analyser in fluid communication with said gas extraction cell for performing gas analysis on the extracted gas sample, said analyser including a photo-acoustic spectroscopy measurement system having an elongated channel including a resonant cavity and an electromagnetic energy source, wherein the resonant cavity includes a first portion and a second portion configured for containing at least part of the gas sample, wherein said first portion of the resonant cavity defines an optical pathway configured for propagation of electromagnetic energy from the electromagnetic energy source, and wherein the resonant cavity includes an element configured for obstructing the propagation of the electromagnetic energy from the electromagnetic energy source through the second portion of the resonant cavity, the photo-acoustic spectroscopy measurement system being configured to excite a portion of the gas sample contained in the optical pathway defined by the first portion of the resonant cavity to produce a photo-acoustic signal associated with the extracted gas sample;

d. a processing unit programmed for deriving information associated with dissolved gas concentrations in the electrical insulating liquid at least in part by processing the photo-acoustic signal produced by the analyser.

In accordance with another aspect, the present disclosure relates to an apparatus for performing dissolved gas analysis on a piece of electrical equipment having components immersed in electrical insulating liquid, the apparatus comprising:
   a. a liquid inlet and a liquid outlet connectable to the piece of electrical equipment for allowing electrical insulating liquid to circulate between the piece of electrical equipment and the apparatus through a liquid circulation path;
   b. a gas extraction cell in communication with the liquid circulation path, said gas extraction cell being configured for extracting a gas sample from the electrical insulating liquid, said gas extraction cell including a pressure regulating element for mixing an external gas with the gas sample extracted from the electrical insulating liquid to obtain a mixed-gas sample, wherein the mixed-gas sample has a pressure approaching a target pressure;
   c. an analyser in fluid communication with said gas extraction cell for performing gas analysis on the extracted gas sample, said analyser including a photo-acoustic spectroscopy measurement system having an elongated channel including a resonant cavity and an electromagnetic energy source, the photo-acoustic spectroscopy measurement system being configured to contain and excite the extracted gas sample to produce a photo-acoustic signal associated with the extracted gas sample;
   d. a processing unit programmed for deriving information associated with dissolved gas concentrations in the electrical insulating liquid at least in part by processing the photo-acoustic signal produced by the analyser.

In accordance with another aspect, the present disclosure relates to a method for performing dissolved gas analysis on a piece of electrical equipment having components immersed in electrical insulating liquid in an apparatus that is connectable to the piece of electrical equipment for allowing electrical insulating liquid to circulate between the piece of electrical equipment and the apparatus through a liquid circulation path, the method comprising:
   a. causing electrical insulating liquid to be directed to a gas extraction cell in communication with the liquid circulation path to partially fill the gas extraction cell;
   b. waiting certain period of time to allow a gas sample from the electrical insulating liquid to accumulate in a head space of the gas extraction cell;
   c. using a pressure regulating element to introduce an external gas to the gas sample extracted from the electrical insulating liquid to obtain a mixed-gas sample in the head space of the gas extraction cell, wherein the obtained mixed-gas sample has a pressure approaching a target pressure;
   d. performing gas analysis on the mixed-gas sample including using a photo-acoustic spectroscopy measurement system to produce a photo-acoustic signal associated with the mixed-gas sample
   e. deriving information associated with dissolved gas concentrations in the electrical insulating liquid at least in part by processing the photo-acoustic signal.

In accordance with another aspect, the present disclosure relates to an apparatus for performing dissolved gas analysis on a piece of electrical equipment having components immersed in electrical insulating liquid, the apparatus comprising:
   a. a liquid inlet and a liquid outlet connectable to the piece of electrical equipment for allowing electrical insulating liquid to circulate between the piece of electrical equipment and the apparatus through a liquid circulation path;
   b. a gas extraction cell in communication with the liquid circulation path, said gas extraction cell being configured for extracting a gas sample from the electrical insulating liquid;
   c. an analyser in fluid communication with said gas extraction cell for performing gas analysis on the extracted gas sample, said analyser including a photo-acoustic spectroscopy measurement system having an elongated channel including a resonant cavity and an electromagnetic energy source, the photo-acoustic spectroscopy measurement system being configured to contain and excite the gas sample contained in the optical pathway defined by the first portion of the resonant cavity to produce a photo-acoustic signal associated with the gas sample at least in part by producing a periodically pulsed beam of electromagnetic radiation having a chopping frequency greater than or equal to 150 Hz;
   d. a processing unit programmed for deriving information associated with dissolved gas concentrations in the electrical insulating liquid at least in part by processing the photo-acoustic signal produced by the analyser.

In accordance with another aspect, the present disclosure relates to an apparatus for performing dissolved gas analysis on a piece of electrical equipment having components immersed in electrical insulating liquid, the apparatus comprising:
   a. a liquid inlet and a liquid outlet connectable to the piece of electrical equipment for allowing electrical insulating liquid to circulate between the piece of electrical equipment and the apparatus through a liquid circulation path;
   b. a gas extraction cell in communication with the liquid circulation path, said gas extraction cell being configured for extracting a gas sample from the electrical insulating liquid;
   c. an analyser in fluid communication with said gas extraction cell for performing gas analysis on the extracted gas sample, said analyser including a photo-acoustic spectroscopy measurement system having an elongated channel including:
      i. a resonant cavity;
      ii. an electromagnetic energy source;
      iii. a device configured for measuring pressure variations in said resonant cavity to generate a photo-acoustic signal associated with the extracted gas sample; and
      iv. an optical chopper;
   d. the photo-acoustic spectroscopy measurement system being configured to contain and excite the extracted gas sample to produce a photo-acoustic signal associated with the gas sample, the electromagnetic radiation source and the optical chopper operating in cooperation for producing a periodically pulsed beam of electromagnetic radiation, said photo-acoustic spectroscopy measurement system including one or more damper elements for reducing vibrational interferences between the optical chopper and the device for measuring pressure variations;
   e. a processing unit programmed for deriving information associated with dissolved gas concentrations in the electrical insulating liquid at least in part by processing the photo-acoustic signal produced by the analyser.

It is to be understood that the equipment that serves in the generating, transmitting, and distributing of electrical power, as referred to in the present description, refers to transformers (sometimes called oil-immersed transformers), tap-changers and circuit breakers, and/or any other electrical asset for which detecting/measuring a gas dissolved in insulating liquid may be used as an indication of fault detection/diagnosis of the equipment.

In the present description, it is also to be understood that the term "gas" can refer to a plurality of gases and/or may embrace the term "vapour".

All features of exemplary embodiments which are described in this disclosure and are not mutually exclusive can be combined with one another. Elements of one embodiment or aspect can be utilized in the other embodiments/aspects without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific exemplary embodiments is provided herein below with reference to the accompanying drawings in which.

Figure 1:
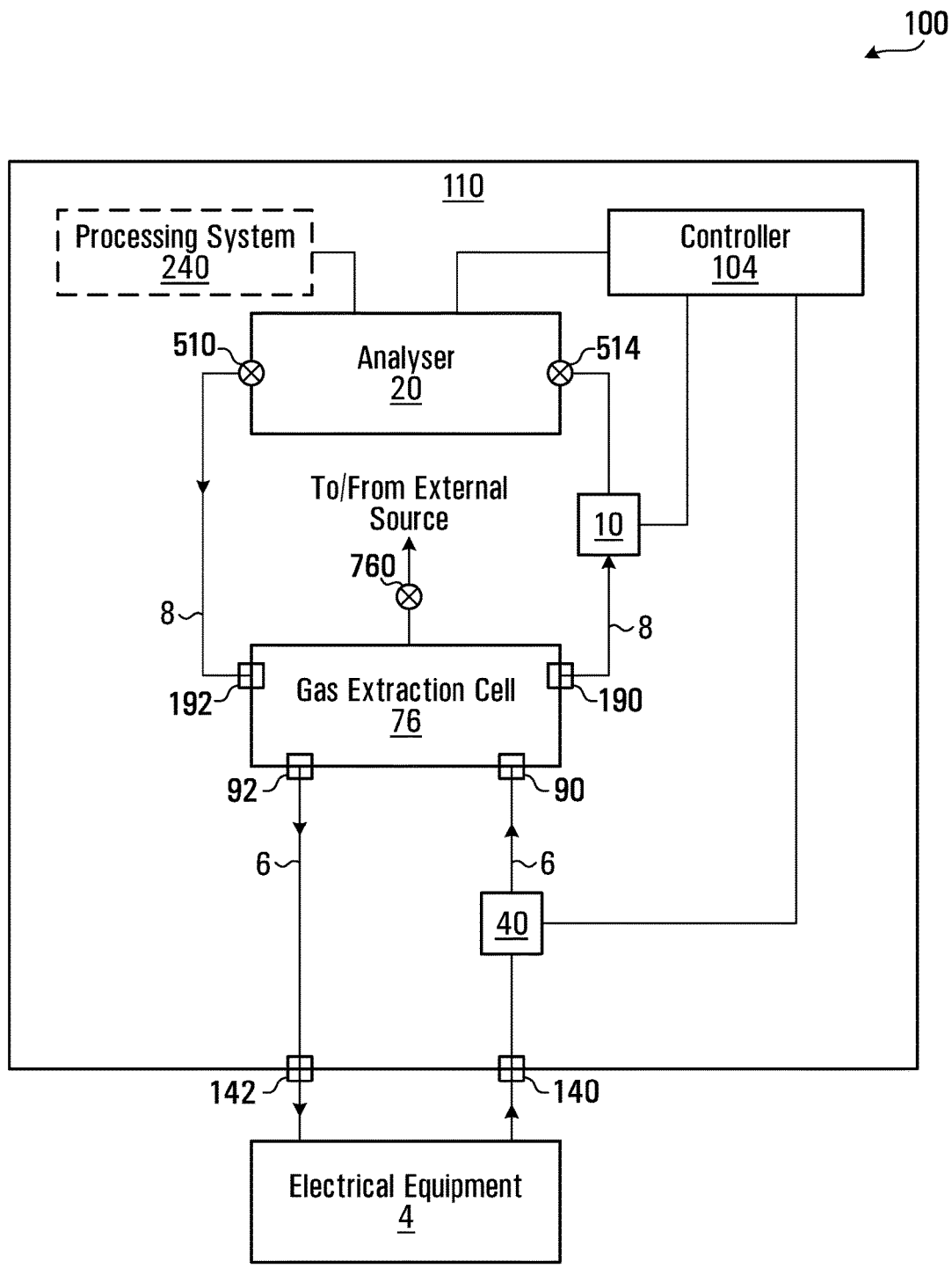
FIG. 1 is a functional block diagram of a dissolved gas analysis (DGA) apparatus 100 connected to a piece of electrical equipment 4, wherein the DGA apparatus 100 includes an analyser 20 in fluid communication with a gas extraction cell 76, a controller 104 and a processing system 240, in accordance with a non-limiting example of implementation of the present invention.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION OF EMBODIMENTS

A detailed description of one or more embodiments of the invention is provided below along with accompanying Figures that illustrate principles of the invention. The invention is described in connection with such embodiments, but the invention is not limited to any specific embodiment. The scope of the invention is limited only by the claims. Numerous specific details are set forth in the following description in order to provide a thorough understanding of the invention. These details are provided for the purpose of non-limiting examples and the invention may be practiced according to the claims without some or all of these specific details. For the purpose of clarity, technical material that is known in the technical fields related to the invention has not been described in great detail so that the invention is not unnecessarily obscured.

The description below is directed to a specific implementation of the present invention in the context of dissolved gas analysis (DGA) applications using photo-acoustic spectroscopy (PAS) for detecting/measuring a gas dissolved in electrical insulating liquid of that type that may be used for example in transformers, tap-changers and circuit breakers.

Photo-acoustic spectroscopy has been known since 1880, when it was discovered by Alexander Graham Bell. Photo-acoustic spectroscopy includes illuminating a sample contained in a closed gas-filled cell with pulsed electromagnetic radiations and measuring the resultant acoustic signal. It is well understood that each gas has an individual infrared (IR) absorption spectrum and the level of absorption is generally directly proportional to the gas concentration. When a gas absorbs electromagnetic radiation (e.g., IR light), the temperature of the gas will increase and, if it is held in a sealed container, this will result in a proportional rise in pressure. When the infrared signal is then pulsed at an audible rate the resultant pressure wave, or acoustic signal, is directly proportional to the concentrations within the sealed measurement chamber. Devices configured for measuring pressure variations in the resonant cavity (such as, for example, sensitive microphones and/or pressure sensor) are used in such apparatus to convert the acoustic wave pressure into electrical sound signals which can be further amplified using lock-in amplifiers or other methods.

One practical implementation of the invention includes detecting/diagnosing faults in electrical equipment that serves in the generation, transmission and/or distribution of electrical power for example, but not limited to, a transformer, a tap-changer or a circuit breaker, having components immersed in electrical insulating liquid, such as electrical insulating oil. In such practical implementation, the dissolved gas analysis can provide near real-time insight into the condition of the electrical equipment by identifying and quantifying fault gases which are dissolved in the insulating liquid of the electrical equipment. Moreover, such dissolved gas analysis can assist in early detection of electrical equipment faults, minimizing costly unplanned outages and equipment failure. Examples of electrical equipment faults, such as power transformers faults, can include arcing, partial discharge and overheating (pyrolysis).

Dissolved Gas Analysis Apparatus

A specific example of implementation of a dissolved gas analysis apparatus 100 is shown in the block diagram of FIG. 1.

In this example, the apparatus 100 includes a housing 110 which encloses various elements for performing dissolved gas analysis on a piece of electrical equipment 4 having components immersed in electrical insulating liquid, such as electrical insulating oil for example. The housing 110 can be made of any suitable material including but not limited to plastic, metal or a composite.

In a specific practical implementation, the apparatus 100 can be configured to be portable and be embodied in a housing 110 of a compact size dimensions and weight such that the apparatus 100 can be used as a portable apparatus connectable to a piece of electrical equipment 4 containing electrical insulating liquid when a DGA operation is desired. In another specific practical implementation, the apparatus 100 is configured to be a fixed/stationary device, which is connected to the piece of electrical equipment 4 containing electrical insulating liquid and can be left connected to the piece of electrical equipment 4 for an extended length of time. In such cases the housing 110 of the apparatus may be configured to be securely mountable upon a supporting surface, such as a wall or frame, for example by providing suitable mounting elements and/or suitable fasteners on the housing 110 to facilitate such mounting.

As depicted, the apparatus 100 includes a liquid inlet 140 and a liquid outlet 142 connectable to the piece of electrical equipment 4 for allowing electrical insulating liquid to circulate between the piece of electrical equipment 4 and the apparatus 100 over a liquid circulation path 6, which transfers insulating liquid in and out of the apparatus 100.

The apparatus 100 further includes a gas extraction cell 76 in communication with the liquid circulation path 6. The gas extraction cell 76 is configured for extracting a gas sample from the electrical insulating liquid. In some specific practical implementations, the gas extraction cell 76 may be configured for holding a sample of the electrical insulating liquid from the piece of electrical equipment 4 in order to extract a gas sample from that oil sample or, alternatively, the gas extraction cell 76 may be configured for extracting a gas sample as the electrical insulating liquid travels through the liquid circulation path 6. It is to be appreciated that the insulating liquid traveling through the liquid circulation path 6 may include dissolved gases and gas bubbles. A more detailed description of the gas extraction cell 76 and its operation is provided later in this text.

The apparatus 100 also includes an analyser 20 in fluid communication with the gas extraction cell 76 over fluid circulation path 8 for performing gas analysis on the gas sample extracted from the sample of the electrical insulating liquid by the gas extraction cell 76. The fluid circulation path 8 allows fluid travel from the extraction cell 76 to the analyser 20 as well as from the analyser 20 to the extraction cell 76. In other words, in the specific example depicted, the fluid circulation path 8 creates a closed loop configuration between the analyser 20 and the gas extraction cell 76 for the sample gas to travel through. An advantage of a closed loop configuration is that it may accelerate the speed at which equilibration of gas concentrations between the extraction cell 76 and the gas analyser 20 is reached. A more detailed description of the analyser 20 and its operation is provided later in this text. While the examples depicted and described in the present description show closed loop configurations, it is to be appreciated by the person skilled in the art that, in alternate implementations (not shown), e.g., a single connecting conduit between the gas extraction cell 76 and the analyser 20 may instead be used.

The apparatus 100 further includes one or more suitable pumps 10 for causing and controlling a flow of gas along the fluid circulation path 8, in and out of the analyser 20. While a specific location for one pump 10 along the fluid circulation path 8 is shown in FIG. 1, it will be apparent to the person of skill that other locations and/or more than one pump 10 may be present depending on specific implementations.

The apparatus 100 further includes a suitable pump 40 for controlling a flow of liquid in the liquid circulation path 6 from the piece of electrical equipment 4 to the apparatus 100 and through the gas extraction cell 76. It will be apparent to the person of skill that other locations for the pump 40 may be suitable for this purpose.

The apparatus 100 further includes a controller 104 for controlling the operations of the different features/components of the apparatus 100. In specific practical implementations, the controller 104 includes suitable hardware and/or software for controlling the operational settings of the different features of the apparatus 100, including the pumps 40 and 10 and valves (not shown) for controlling the flow of insulating liquid and gas samples (through liquid circulation path 6 and fluid circulation path 8) and the operations of analyser 20. In some specific practical implementations, the controller 104 may receive electrical power from an electric power source that is connected to the controller 104 via service wiring (not shown). The controller 104 may be configured in different suitable manners, which will become apparent to the person skilled in the art in view of the present description and thus will not be described in further detail here.

In addition, the apparatus 100 may further include a processing system 240 programmed for processing signals generated by the analyser 20 to derive, amongst other, information conveying concentrations of specific gas species present in the insulating liquid and/or to derive information conveying a fault status (or alternatively a fault level ranking) of the electrical equipment 4.

The following sections of this text will describe in greater detail various features of the apparatus 100 and the manner in which they may interact with one another in specific implementations.

Analyser 20

The analyser 20 is in fluid communication with the gas extraction cell 76 over fluid circulation path 8 for performing gas analysis on the gas sample extracted from the sample of the electrical insulating liquid by the gas extraction cell 76 to produce a photo-acoustic signal associated with the gas sample. In specific practical implementations the analyser is configured for producing a signal conveying concentration information of one of more of the following fault gases: carbon dioxide ($CO_2$), carbon monoxide (CO), ethane ($C_2H_6$), methane ($CH_4$), ethylene ($C_2H_4$), acetylene ($C_2H_2$) and sulfur hexafluoride ($SF_6$).

The analyser 20 includes a number of elements for performing the gas analysis on the gas sample extracted from the sample of electrical insulating liquid.

For example, the analyser 20 includes a photo-acoustic spectroscopy (PAS) measurement system 200 (e.g., shown in FIG. 2), which is configured to contain and excite the gas sample extracted from the electrical insulating liquid in the gas extraction cell 76. Upon exciting the gas sample, the PAS measurement system 200 is also further configured for generating a signal which conveys information associated with the gas sample. A more detailed description of the photo-acoustic measurement system 200 and its operation is provided later in this text.

The analyser 20 may be in communication with the processing system 240, which may be programmed for processing the photo-acoustic signal generated by the PAS measurement system 200 conveying information associated with the gas sample to derive information conveying concentrations of specific gas species present in the insulating liquid and/or to derive information conveying a fault status (or alternatively a fault level ranking) of the electrical equipment 4. In a specific implementation, the fault status may convey the presence (or absence) of a detected fault associated with the electrical insulating liquid in the electrical equipment 4, such as for example an excess concentration in one or more of certain specific fault gases. In some specific implementation, which may be used instead of the fault status or in combination therewith, a fault level ranking may be derived to convey on a graded scale a level of criticality in connection with the derived excess concentrations of certain specific fault gases. The specific scale used may vary from one implementation to the other and is not critical to the present invention and thus will not be described in further detail here.

In some specific practical implementation, the processing system 240 may be configured for comparing a derived concentration of a specific target fault gas in the insulating liquid to a reference range of concentrations for that fault gas in order to identify potential deviations from expected measurements and detect potential on-going or developing faults in the electrical equipment 4. It is to be appreciated that a detected potential on-going or developing fault in the electrical equipment 4 may be expressed in absolute terms (for example a fault is or is not present) or alternatively as a gradated fault level ranking conveying how far from an expected concentration range the measurement of the specific target fault gas is.

The processing system 240 may be further programmed for generating a signal for causing the information conveying the fault status (or alternatively a fault level ranking) of the electrical equipment 4 and/or the derived information conveying concentration of specific gas species present in the insulating liquid to be displayed on a display device. The display device may be comprised of any suitable visual elements including a display screen, a series of lighting elements (e.g. light-emitting diodes (LEDs)) or any other suitable element that may suitably convey the information to a human operator. In some embodiments, the display device may be part of the apparatus 100 or, alternatively, the display device may reside in a computing device (not shown in the figures) located remotely from the apparatus 100 wherein the computing device is in communication with the apparatus 100 over a data communication link.

It will be apparent to the reader that, in some embodiments, the processing system 240 functionality may be embodied, in whole or in part, on a processing assembly including suitable hardware and/or software components physically located within the apparatus 100. In such embodiment, the processing system 240 may be in communication with the analyser 20 (over circuit wiring for example) for receiving a photo-acoustic signal generated by the PAS measurement system 200 of the analyser 20 which conveys information associated with the gas sample to derive information conveying concentrations of specific gas species present in the insulating liquid and/or to derive information conveying a fault status (or alternatively a fault level ranking) of the electrical equipment 4. The processing system 240 may also be connected to a display device (not shown) part of the apparatus 100 and may be programmed for causing the display of the information conveying the fault status (or alternatively a fault level ranking) of the electrical equipment 4 and/or the derived information conveying concentration of specific gas species present in the insulting liquid.

In an alternative implementation, the processing system 240 may instead be embodied, in whole or in part, on a processing assembly including suitable hardware and/or software components physically located remotely from the apparatus 100. In such embodiment, the processing system 240 may be located in a remote computing device in communication with to the apparatus 100 over a short-range wireless connection or over a private or public (Internet) computer network. In such cases, it will become apparent to the person of skill in the art that the apparatus 100 would be equipped with suitable network interface hardware and software for establishing communications with the remote computing device.

In yet another alternative implementation, the processing system 240 functionality may be performed in whole or in part "in the cloud" (not shown) to derive information conveying concentrations of specific gas species present in the insulting liquid and/or to derive information conveying a fault status (or alternatively a fault level ranking) of the electrical equipment 4.

Cloud computing has, amongst other, the advantage of allowing the specific processes (including the software) used to derive useful information to be modified and/or upgrades as well as new functionality to be introduced in one centralized location and thus without requiring access to the individual physical apparatus 100. For entities making use of a large number of apparatuses 100, this may result in significant time savings and associated cost savings.

A more detailed description of the processing system 240 and the functionality that it may provide in some implementations is provided later in this text.

PAS Measurement System

Figure 2:
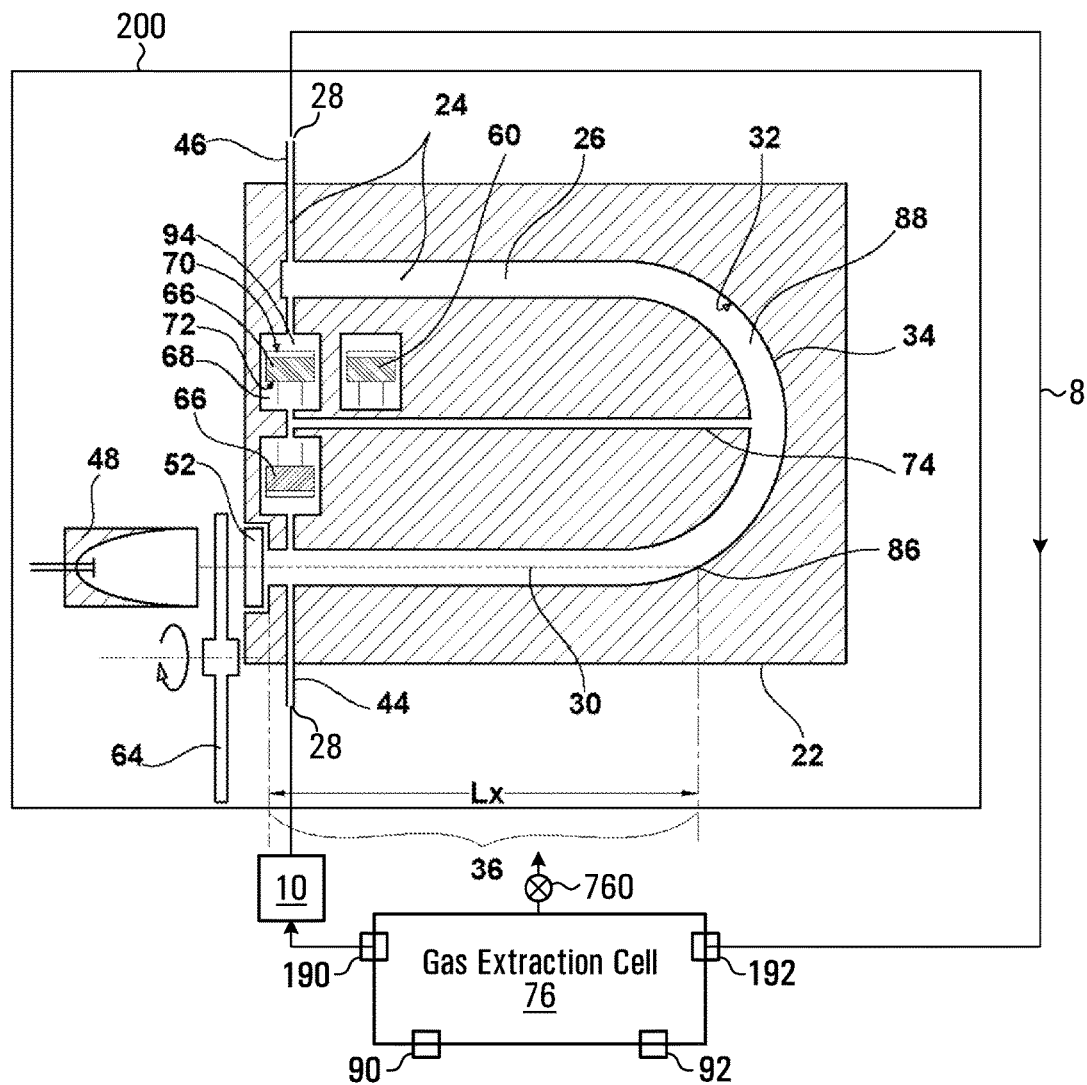
FIG. 2 shows a more detailed block diagram of a photo-acoustic spectroscopy (PAS) measurement system for use in connection with the analyser 20 of the DGA apparatus 100 of FIG. 1 in accordance with a first specific non-limiting example of implementation of the present invention.
Figure 3:
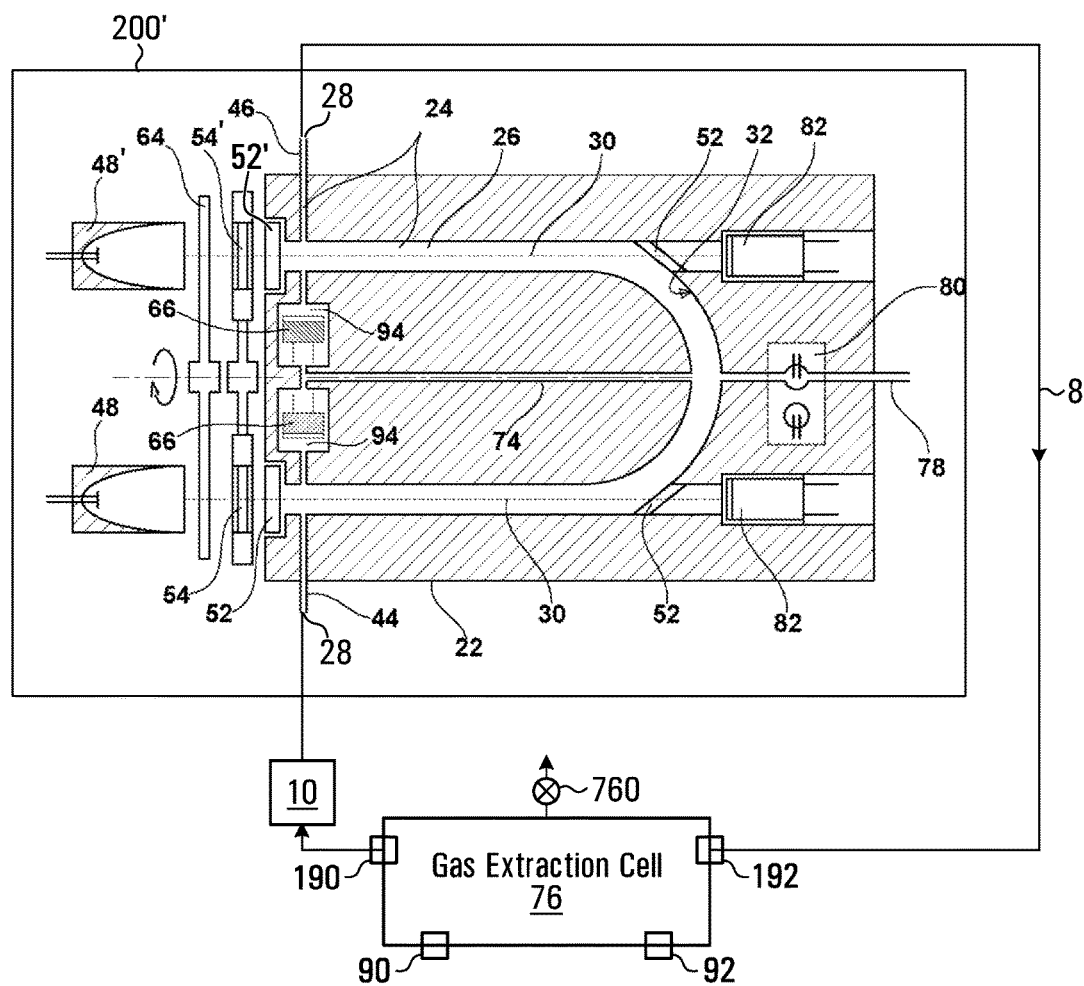
FIG. 3 shows a more detailed block diagram of a photo-acoustic spectroscopy (PAS) measurement system for use in connection with the analyser 20 of the DGA apparatus 100 of FIG. 1 in accordance with a second specific non-limiting example of implementation of the present invention.

FIG. 2 shows a block diagram of a first practical implementation of a PAS measurement system 200 of the analyser 20, which is in fluid communication with the gas extraction cell 76 over fluid circulation path 8. FIG. 3 shows a block diagram of a second practical implementation of a PAS measurement system 200' of the analyser 20, which is in fluid communication with the gas extraction cell 76 over fluid circulation path 8. For the purpose of simplicity, elements of the PAS measurement system 200 and PAS measurement system 200' that are common to one another are being designated with same reference numerals in both figures.

As shown, the PAS measurement system 200 includes a body 22, which can be any rigid enclosing structure for housing components relative to the functionality of the PAS measurement system 200. The body 22 includes inlet 44 and outlet 46 mounted thereon and connecting to fluid circulation path 8 for circulating the gas sample extracted from the electrical insulating liquid by the gas extraction cell 76. It should be noted that the suggested locations of the inlet 44 and the outlet 46 on the body 22 are just exemplifications and, therefore, other connectivity ports and other port locations can be considered. One alternate example of connectivity ports includes gas connection port 78 shown in a second alternative embodiment of a PAS measurement system 200' depicted in FIG. 3 described below.

Turning back to the first practical implementation shown in FIG. 2, the body 22 encloses an elongated channel 24 for containing the gas sample received from the gas extraction cell 76 through the inlet 44. The channel 24 defines an enclosed conduit that is configured for containing the gas sample. The channel 24 includes a section forming a resonant cavity 26 and a section defining a passageway 28 for circulating the gas through the resonant cavity 26. The passageway 28 can be any gas conduit or through hole(s) connecting through inlet 44 and outlet 46 to the fluid path 8 for circulating the gas sample through the resonant cavity 26.

In the specific example depicted, the resonant cavity 26 (also shown in isolated form in FIG. 4) is a hollow-space resonator having a substantially elongated tubular form with a substantially circular cross-section. The length of the resonant cavity 26 is preferably configured in relation to the wavelength of the fundamental frequency of an acoustic standing wave, that is, the smallest natural frequency of the acoustic standing wave inside the resonant cavity 26. The use of such resonator advantageously amplifies the acoustic wave signal, thus, increasing the sensitivity of the analyser 20. More specifically, is particular implementations, the resonant cavity is designed to exhibit an acoustic resonance at a specific frequency of modulation (e.g. pulsating or chopping) of the electromagnetic energy source 48 and thereby increase the signal to noise characteristics of the PAS signal.

The resonant cavity 26 includes a first portion that forms an excitation volume 36 by defining an optical pathway configured for propagation of electromagnetic energy from an electromagnetic energy source 48. In particular, in the configuration depicted in FIG. 2, the excitation volume 36 is a portion of the resonant cavity 26 where pulsed electromagnetic energy 30 originating from the electromagnetic energy source 48 can propagate, thereby exciting the gas sample contained in the excitation volume 36 with the pulsed electromagnetic radiation 30. The resonant cavity 26 also includes a second portion which defines a passive volume 88, where at least a portion of the electromagnetic energy 30 does not propagate into, thereby minimizing excitation of the gas sample contained in the passive volume 88. This can be achieved, for example, by including an element 86 configured for obstructing the propagation of the electromagnetic energy 30 from the first portion through to the second portion of the resonant cavity 26. The excitation volume 36 has an excitation zone length Lx, which can be generally defined between a location where the electromagnetic energy 30 enters the resonant cavity 26 at one end portion of the excitation volume 36 and a location defined by the element configured for obstructing the propagation of the electromagnetic energy 30 at the other end portion of the excitation volume 36. In other words, the excitation volume 36 defines an optical pathway of length Lx configured for propagation of the electromagnetic energy 30.

In one non-limiting embodiment, the excitation zone length Lx is preferably limited to the first half or less of the resonant cavity 26 length, positioned in front of the electromagnetic energy source 48.

In one non-limiting embodiment, the element 86 configured for obstructing the propagation of the electromagnetic energy 30 through to the second portion of the resonant cavity 26 may include a bend 34 in the resonant cavity path at a certain point along the extent of the resonant cavity 26. The bend 34 has a curvature configured for obstructing the propagation of the electromagnetic energy 30 propagating through the resonant cavity 26. The bend 34 can include any angle that can generate a partial or total obstruction to a path of the electromagnetic radiation 30. In a specific practical implementation, the bend 34 may include a 90 degree angle. In another example (of the type depicted in FIG. 2) the bend 34 may form a U-shaped cavity, which may present a more convenient and compact design suitable for some practical implementations.

In another non-limiting embodiment, the element 86 configured for obstructing the propagation of the electromagnetic energy 30 through to the second portion of the resonant cavity 26 may include an absorbing inner wall surface 32 capable of absorbing at least part of the electromagnetic radiation 30.

Obstruction of the electromagnetic energy 30 can be useful in limiting the excitation zone to a zone where the acoustic wave will be mostly in phase with the irradiative excitation generated by the electromagnetic energy source 48.

Figure 4:
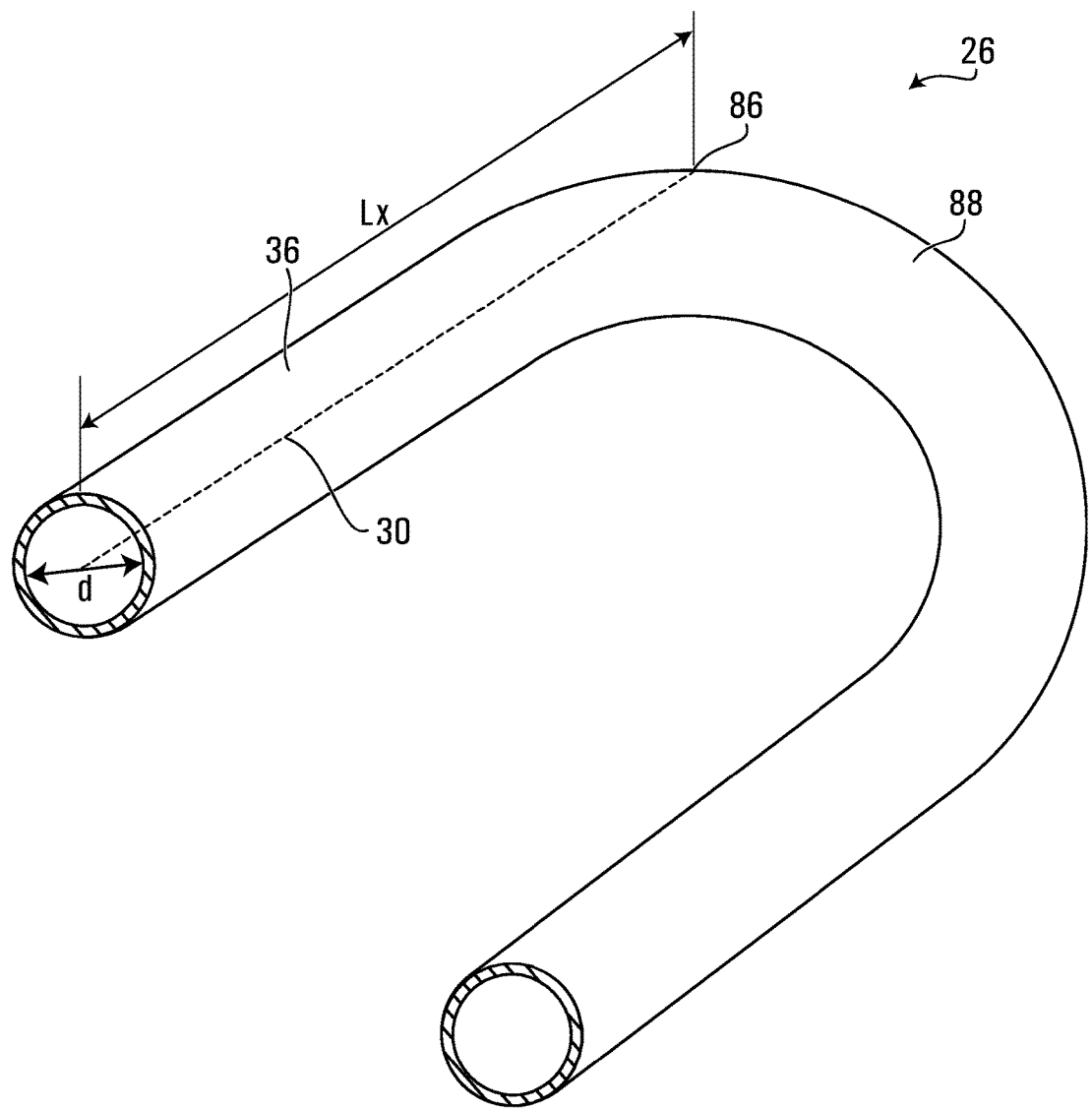
FIG. 4 shows a diagram of a specific practical embodiment of a channel including a resonant cavity for use in connection with the photo-acoustic spectroscopy (PAS) measurement system of FIGS. 2 and 3.

With reference to FIG. 4, the resonant cavity 26 is shown as a U-shaped cavity, which includes two elongated portions and a curved portion linking the two elongated portions, where the first portion of the resonant cavity 26 defining the optical pathway of length Lx is one of the two elongated portions and has an internal diameter d.

In some non-limiting embodiments, the internal diameter size d may vary along the length Lx.

In some alternate embodiments, the internal diameter size d may be substantially of a uniform size along the length Lx.

In the specific embodiments shown in FIGS. 2 to 5, the internal diameter size d is substantially the largest internal diameter size of the channel 24 and remains substantially uniform along its length.

It will be apparent that the embodiments described above, the channel 24 of the PAS measurement system 200 advantageously does not require the presence of buffer volumes.

This provides some advantages in DGA applications for detecting/measuring a gas dissolved in electrical insulating liquid as it reduces the volume of sample gas required to operate the photo-acoustic spectroscopy (PAS) measurement system. Indeed, while the presence of buffer volumes found in conventional PAS measurement systems may afford high sensitivity due to the creation of a pressure wave having maximum amplitude in the center of the resonant cavity (where the sound measuring device is located in these measurement systems) and fixed pressure points in the buffer volumes, these buffer volumes must be filled with sample gas and require longer times to fill with gas having concentrations equilibrated to those in the gas extraction system. The configuration of the channel 24 of the PAS measurement system 200 described above allows omitting buffer volumes, reducing as a result the overall required sample gas volume in the channel, and is thus advantageous from that perspective. The reader is referred to international application no. PCT/CA2016/050511 filed on May 4, 2016 and published on Nov. 17, 2016 (incorporated herein by reference in its entirety) for additional information related to this type of PAS measurement system.

In specific practical implementations, the resonant cavity 26 defining the optical pathway of length Lx may be configured to have a ratio of internal diameter size d to optical pathway length Lx selected from the range of from 0.2 to 0.01; preferably in the range from 0.1 to 0.02. In a specific non-limiting implementation, the ratio is about 0.043.

A resonant cavity 26 having such ratio configuration may present a number of advantages in the context of dissolved gas analysis for pieces of electrical equipment.

For example, the above proposed configuration may allow for a relatively limited inner gas volume to fill the resonant cavity 26 while retaining sufficient optical pathway length Lx to allow obtaining measurements suitable for detecting useful levels and changes in concentration of specific fault gases that the apparatus 100 is designed to test for. Having reduced inner gas volume requirements is advantageous in that, typically, electrical insulating liquid samples taken from electrical equipment yield small volumes of extracted gas samples. For example, the volumes of extracted gas samples are generally of about 10 centimeter cube (cc) or less, or more generally between 3cc and 10cc. It will be appreciated that the larger the required volume of the gas sample, the more time will typically be required to allow a representative gas sample to separate from a liquid sample, particularly if a semipermeable membrane, advantageous in keeping the gas measurement system clean of oil and oil vapours, is used in the gas extraction system. Minimizing gas volume sample requirement to perform the photo-acoustic analysis may thus facilitate obtaining measurements with a better time resolution: less time is required to extract the volume of gas sample necessary to fill the resonant cavity 26 and perform the analysis, which enables performing more frequent analyses over time. Also, for a given analysis time interval, small gas samples may more closely reach equilibrium concentrations with the dissolved gas concentrations in the insulating liquid, offering the possibility to increase accuracy in the dissolved gas measurements.

Additionally, or in the alternative, the above proposed configuration may provide sufficient optical pathway length Lx to allow obtaining signal measurements with resolutions suitable for detecting useful levels or changes in concentration of specific fault gases that the apparatus 100 is designed to test for even given the reduced inner gas volume. In particular, the apparatus 100 (and by extension, the PAS measurement system 200) used for DGA testing of electrical insulating liquid requires the detection of minimal concentrations of certain specific fault gases. In some cases, such minimal concentrations may represent gas concentrations as low as 1 ppm in the case of acetylene. The above proposed ratio configuration for the resonant cavity 26 may effectively reduce the inner gas volume while retaining sufficient optical pathway length Lx to retain the desired detection limits and accuracy of quantification of small concentrations of gases.

Additionally, or in the alternative, the above proposed configuration may facilitate obtaining a well-swept volume for the resonant cavity 26. More specifically, during operation, the resonant cavity 26 is periodically filled with new gas samples over time, possibly including calibration gas or ambient air for background readings. In doing so, a pressure differential is applied to the resonant cavity 26 to move one gas sample out and replace it with a subsequent sample to be characterized. As will be appreciated by the person skilled in the art, during this operation, a certain amount of mixing between the two samples may occur and therefore it is necessary to flow through a slightly greater volume of sample gas than the resonant cavity 26 would hold in order to limit cross-contamination and to ensure that a "pristine" new gas sample is being tested. The flow pattern through an elongated cavity minimizes mixing between successive gas samples, such that gas samples of representative concentrations can be loaded into the cavity with a minimum of total gas flow.

In some particular embodiments, the resonant cavity 26 may further include a reflective inner wall 38 (see for example FIG. 5 and FIG. 6) within the excitation volume 36. In particular, the reflective inner wall 38 is configured for reflecting electromagnetic energy propagating through the excitation volume 36. The reflective inner wall 38 can include a metallic deposit on at least a portion thereof to provide the inner wall with reflective properties. In some non-limiting implementations, the metallic deposit may conveniently include a layer of metal affixed to the inner wall. Various materials may be used for the metal deposit including, without being limited to, tungsten, ruthenium, platinum, silver, tantalum, copper, gold and titanium, among others. In very specific practical embodiments, the metal layer may include gold. However, for certain alternate applications, non-metal materials such as silicon, Teflon™ or other suitable polymer may also be used here, provided the surface reflectivity is sufficient for the intended purpose.

Figure 5:
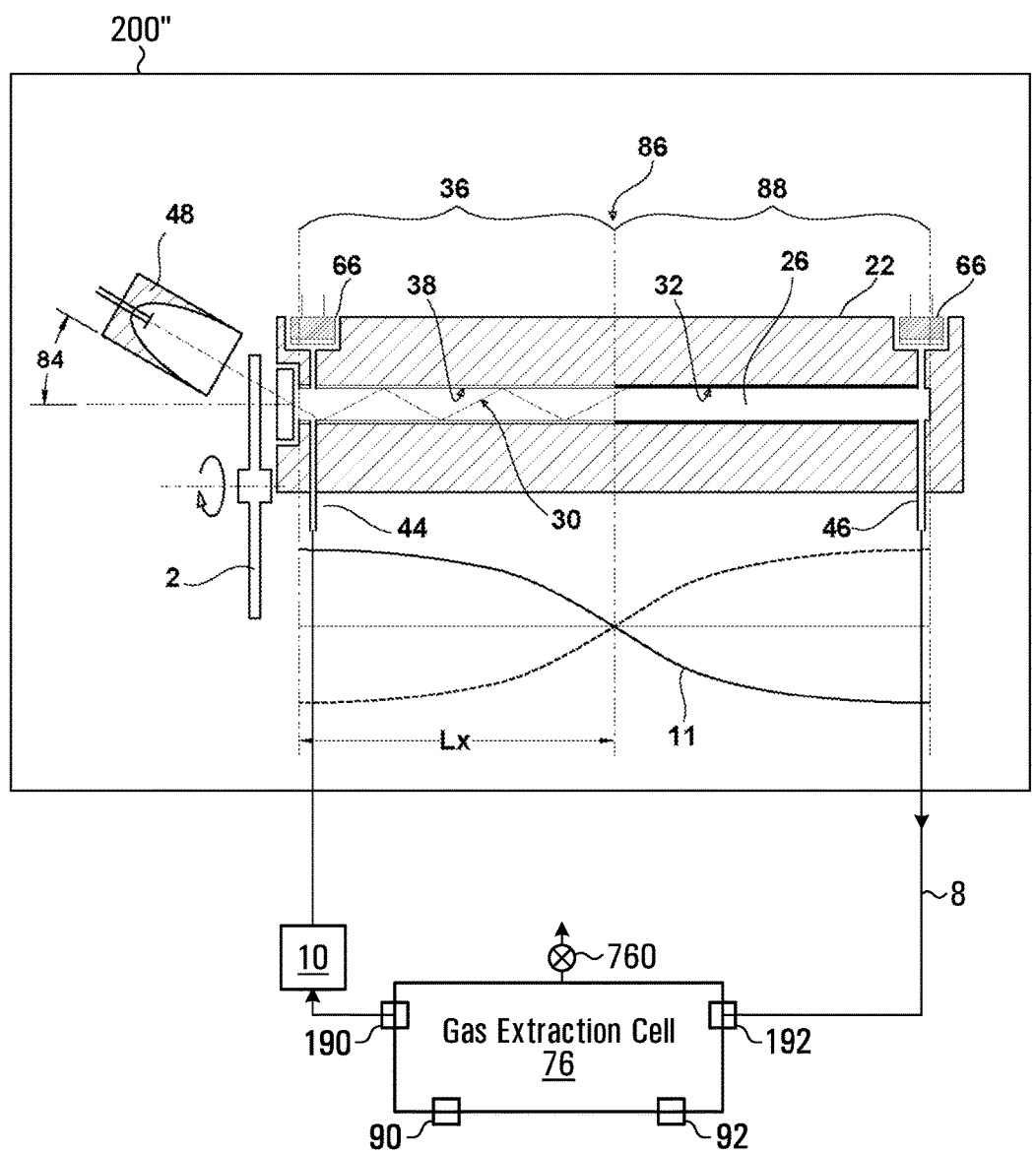
FIG. 5 shows a more detailed block diagram of a photo-acoustic spectroscopy (PAS) measurement system for use in connection with the analyser 20 of the DGA apparatus 100 of FIG. 1 in accordance with a third specific non-limiting example of implementation of the present invention.

FIG. 5 is a block diagram of a third practical implementation of a PAS measurement system 200″, functionally analogous to PAS measurement system 200′ and PAS measurement system 200, and that may be used in the analyser 20 (shown in FIG. 1), which is in fluid communication with the gas extraction cell 76 over fluid circulation path 8. In this embodiment, the resonant cavity 26 is divided into two sections: 1) a reflective section having a reflective inner wall 38, representing the excitation volume 36 and 2) an absorbent section having an absorbing inner wall surface 32 for absorbing electromagnetic radiation and forming a passive volume 88. Electromagnetic energy is at least partially reflected by the reflective inner wall 38 causing the gas sample contained within excitation volume 36 to be excited. The absorbent inner wall surface 32, on the other hand, absorbs at least some of the electromagnetic energy, preferably a substantial amount or all of the electromagnetic energy, and therefore substantially reduces the excitation of the gas in the absorbent section. In this embodiment, the obstruction element 86 can be considered to begin generally at the end of the absorbent section of the resonant cavity 26 that is adjacent to the reflective section. In FIG. 5, for the purpose of simplicity, the obstruction element 86 is shown as being located at the boundary between the reflective section and the absorbent section however it is to be understood that in this embodiment the obstruction element 86 is comprised of the passive volume 88 having an absorbing inner wall surface 32. In this configuration the electromagnetic energy is preferably introduced into the resonant cavity 26 at an incident angle 84 in order to enable the electromagnetic radiation to be reflected by the inner wall and therefore limit propagation of the electromagnetic radiation beyond the radiation obstruction point 86 into the passive volume 88. In practical implementations, the incident angle 84 would be greater than zero and smaller than 90 degrees, for example between 5 and 30 degrees. In FIG. 5 the incident angle 84 can be achieved by tilting the electromagnetic source 48 away from the resonant cavity 26 axis.

Figure 6:
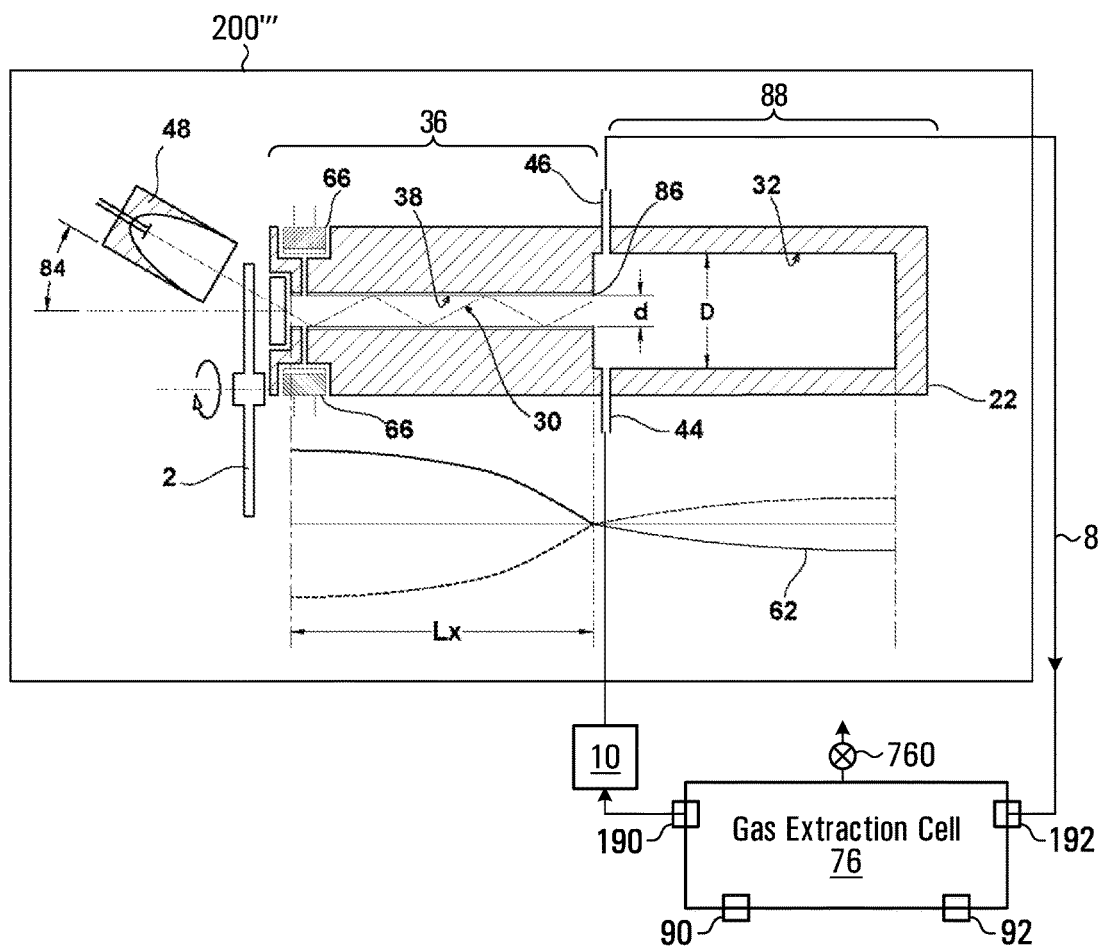
FIG. 6 shows a more detailed block diagram of a photo-acoustic spectroscopy (PAS) measurement system for use in connection with the analyser 20 of the DGA apparatus 100 of FIG. 1 in accordance with a fourth specific non-limiting example of implementation of the present invention.

FIG. 6 shows a block diagram of a fourth practical implementation of a PAS measurement system 200''', functionally analogous to PAS measurement systems 200 200' and 200", and that may be used in the analyser 20 (shown in FIG. 1), which is in fluid communication with the gas extraction cell 76 over fluid circulation path 8. The embodiment of FIG. 6 is similar to that of FIG. 5 however, rather that maintaining a substantially uniform internal diameter over the length of the resonant cavity, the internal diameter D of the section of the resonant cavity forming the passive volume 88, and which includes an absorbing inner wall surface 32 for absorbing electromagnetic radiation, is bigger than the internal diameter d of the section of the resonant cavity forming the excitation volume 36. Increasing the cross-sectional area of the passive volume 88 may result in lowering the amplitude of the sound wave 62 inside the passive volume 88. This may reduce anti-phase excitation which may occur inside the passive volume 88 due to some electromagnetic radiation propagating beyond the obstruction element 86 into the passive volume 88. In this embodiment, the obstruction element 86 can be considered to begin generally at the end of the section of the resonant cavity forming the passive volume 88 that is adjacent to the section of the resonant cavity forming the excitation volume 36. In FIG. 6, for the purpose of simplicity, the obstruction element 86 is shown as being located at the boundary between the reflective section and the absorbent section however it is to be understood that in this embodiment the obstruction element 86 is comprised of the passive volume 88 having an absorbing inner wall surface 32 and the larger diameter D.

In some practical implementations, the photo-acoustic measurement system 200 may further include gas-transfer control elements to shut off, release, dose, distribute or mix gas fluids. Such gas-transfer control elements can be conveniently associated with and located along any of the fluid conduits, for example passageway 28 and/or channel 24 to control gas transfer into/out of the passageway 28 and/or the channel 24. In a specific practical implementation, such gas-transfer control elements may include one or more control valves.

Figure 7A:
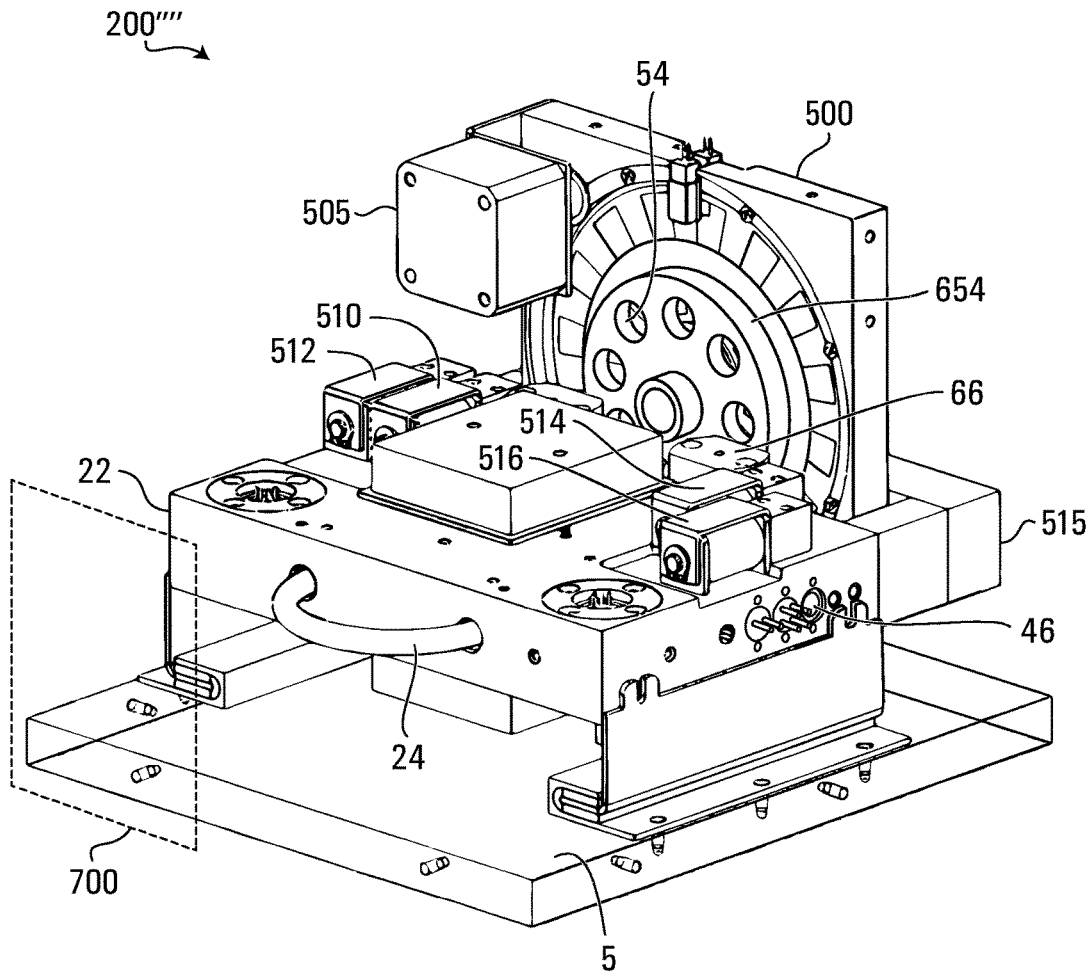
FIG. 7A shows a top front isometric view of a specific practical implementation of a photo-acoustic spectroscopy (PAS) measurement system suitable for use in the analyser 20 of the DGA apparatus of FIG. 1 in accordance with a non-limiting example of implementation of the present invention.
Figure 7B:
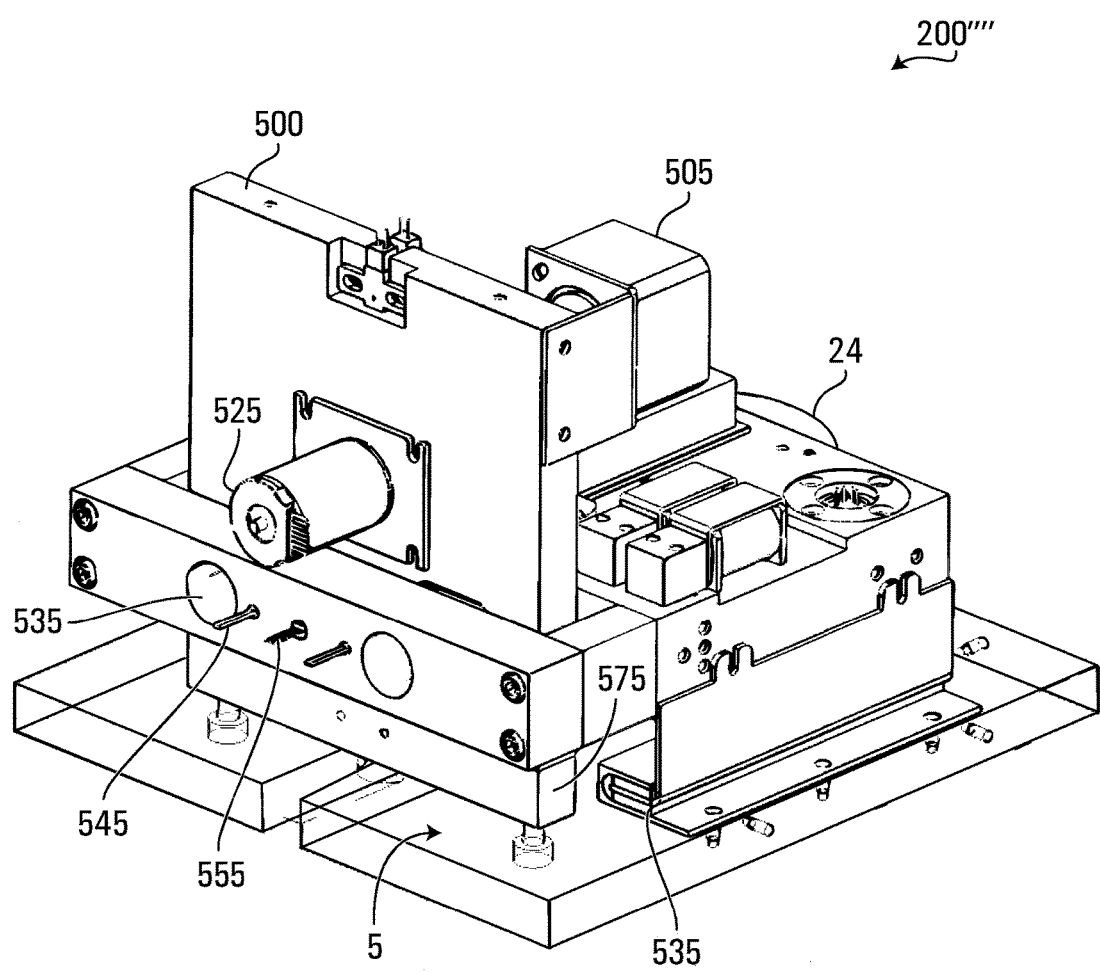
FIG. 7B shows a top rear isometric view of the photo-acoustic spectroscopy (PAS) measurement system of FIG. 7A.

FIGS. 7A and 7B show isometric views of a specific practical implementation of a photo-acoustic spectroscopy (PAS) measurement system 200" suitable for use in the analyser 20 of the DGA apparatus of FIG. 1 in accordance with a non-limiting example of implementation of the present invention. FIG. 7A shows control valves 510, 512, 514, 516 which are associated with and located along the passageway 28 and/or with the channel 24 to control gas transfer into/out of the passageway 28 and/or the channel 24. In specific examples, such control valves may be solenoid valves or any other suitable type of valves.

The photo-acoustic measurement system 200 also includes at least one electromagnetic source 48 (shown as being encased in chamber 535 in FIG. 7B) for generating electromagnetic energy 30, whereby the electromagnetic energy has wavelengths capable of being absorbed by the specific target gas whose concentration is to be measured inside the resonant cavity 26, more particularly in the excitation volume 36.

The electromagnetic source 48 may comprise a laser radiation source, an LED source, an incandescent lamp assembly or the like. In the specific embodiment shown in FIGS. 7A and 7B, the electromagnetic source 48 is conveniently embodied in an electromagnetic source block 515.

The selection of the type and characteristic of the electromagnetic energy source 48 depends on the specific target gases whose concentration is to be measured. A target gas will have maximum absorbance of electromagnetic energy 30 at specific wavelengths. Preferably, the photo-acoustic analyser 20 employs a suitable infrared (IR) electromagnetic energy source.

In some embodiments, at least one optical window 52 (see FIG. 2) is associated with the at least one electromagnetic source 48 for introducing the electromagnetic energy 30 into the resonant cavity 26. The optical window 52 refers to one or more apertures, openings, transparent or translucent portions of the body 22 of the photo-acoustic spectroscopy (PAS) measurement system 200 allowing transmission of the electromagnetic energy 30 into the resonant cavity 26.

In some embodiments, the photo-acoustic measurement system 200 also includes at least one optical lens (not shown) mounted between the at least one electromagnetic source 48 and the at least one optical window 52 for focusing the electromagnetic energy 30 into the resonant cavity 26. The lens can also direct the electromagnetic energy 30 inside the resonant cavity 26.

Referring to FIG. 7B, in specific embodiments, the photo-acoustic measurement system 200 may also include a temperature sensor 555 and heater 545 to improve stability of the IR source by having it mounted into a temperature controlled block.

Sound Measuring Devices

The photo-acoustic measurement system 200 shown in FIG. 2 also includes at least one sound measuring device 66 having a sensing input for detecting variations in pressure inside the resonant cavity 26, and an output for generating a signal indicative of the pressure variations which is representative of a concentration of a specific target gas being detected. The sound measuring device 66 has first 70 and second 72 opposite surfaces. The first surface 70 is a sensing surface facing the sensing chamber 94 which is connected to the resonant cavity 26.

In operation, the absorption of the electromagnetic energy 30 by the sample gas in the resonant cavity 26 heats up the gas inside the excitation volume 36 and therefore generates a pressure wave inside the resonant cavity 26. The pressure wave includes pressure variations that are picked up by the sensing input of the sound measuring device 66. Thus the sound measuring device 66 is configured for measuring pressure variations in the resonant cavity 26 to generate a photo-acoustic signal associated with the extracted gas sample.

Some practical sound measuring devices require an average pressure around the first surface 70 of the sound measuring device 66 to be substantially equal with an average pressure around the second surface 72 of the sound measuring device 66. For such practical implementation, the PAS body 22 may include at least one pressure chamber 68 for housing the at least one sound measuring device 66 and a pressure equalisation duct 74 fluidly connecting the resonant cavity 26 and the at least one pressure chamber 68, nearby the second surface 72 of the at least one sound measuring device 66. The pressure equalisation duct 74 regulates the average pressure inside the pressure chamber 68.

As shown in FIG. 2, the photo-acoustic measurement system 200 can also include an auxiliary sound measuring device 60 mounted inside the PAS body 22 and proximate to the at least one sound measuring device 66 for detecting background noise and generating a signal indicative of the background noise. For background noise cancellation, the signal indicative of the background noise can be subtracted from the signal indicative of the pressure signal. Advantageously, the background noise cancelation may improve the detection sensitivity of the analyser 20.

Optionally as a variant, the acoustic coupling between the resonant cavity 26 and the sound measuring device 66 can be improved by making the sensing chamber 94, a resonant cavity, resonating at similar frequencies as the resonant cavity 26. For example, the sensing chamber 94 may resemble a Helmholtz resonator having the "nipple" connected to the resonant cavity 26.

Pulsed Electromagnetic Radiations

When the electromagnetic energy source 48 in the photo-acoustic measurement system 200 (or in 200' 200'' and 200''') produces non-pulsed electromagnetic radiations (e.g., infra-red radiations), the photo-acoustic measurement system 200 may conveniently include a feature, such as an optical chopper 64, operating in cooperation with the electromagnetic source 48 for producing pulsed radiations. Such features are known in the art and may include, for example, a rotating perforated wheel chopper.

Referring to FIG. 2, the optical chopper 64 is shown to be a rotating perforated wheel chopper mounted between the electromagnetic source 48 and the optical window 52 and is operated by chopper motor 525 (as shown in FIG. 7B). The optical chopper 64 is preferably operated at a frequency selected in relation to the length of the resonant cavity 26. The optical chopper 64 can be any device capable of periodically interrupting the electromagnetic energy 30 originating from the electromagnetic source 48 from flowing into the resonant cavity 26.

Referring to FIG. 3, an alternative configuration of an optical chopper 64' is shown, analogous to optical chopper 64. Optical chopper 64' is also a rotating perforated wheel chopper mounted between two electromagnetic sources 48 and respective optical windows 52 and is operated by chopper motor 525 (as shown in FIG. 7B). The optical chopper 64' is preferably operated at a frequency selected in relation to the length of the resonant cavity 26. The optical chopper 64' can be any device capable of periodically interrupting the electromagnetic energy 30 originating from the electromagnetic sources 48 from flowing into the resonant cavity 26.

Alternatively, the electromagnetic source 48 used in photo-acoustic measurement system 200 (as well as 200' 200'' 200''') can be of a pulsating radiation source for providing pulsed electromagnetic energy 30 into the resonant cavity 26. In specific embodiments in which the electromagnetic source 48 is a pulsating radiation source, the optical chopper 64 may be omitted.

In some specific practical implementations, the photo-acoustic measurement system 200 is driven to excite an acoustic resonance using an acoustic chopping frequency (or pulse frequency) that is greater than traditional photo-acoustic applications. In particular, while operating, electrical equipment such as power transformers generate mechanical vibrations having primary frequencies in the range of 100 Hz to 120 Hz. These vibrations sometimes generate a sound (a "hum"), which may in some cases interfere with the sensors used in PAS measurement systems. In addition to these vibrations, many other sources of ambient noise and industrial noise decrease steadily with frequency.

It has been found that by operating the photo-acoustic measurement system 200 at frequencies above that of the mechanical vibrations of the electrical equipment (in other words above 100-120 Hz), improved signal-to-noise ratios can be achieved as the amplitude of vibration that may be transmitted to the analyser is less, thereby yielding improved sensitivity of the analyser 20 to detect small concentrations of fault gases. While conventional PAS measurement systems may operate at chopping frequencies below 50 Hz, in specific practical embodiments of the present invention, the acoustic chopping frequency (for example as effected by the chopper 64) (or pulsating frequency) used is set to be above 150 Hz, for example at a value in a range between 150 Hz and 4000 Hz; preferably in a range between 200 Hz and 2000 Hz and most preferably still in a range between 500 Hz and 1000 Hz to limit interferences with noise sources in the lower frequency ranges. In a specific non-limiting practical implementation, an optical chopping frequency of about 750 Hz has been found to provide good signal-to-noise ratio.

It will be appreciated that, in practical implementations, the acoustic resonance of the channel, the devices for measuring pressure variations, electronics and software of the analyser 20 are configured to reject signals having frequencies that materially differ from the chopping (pulsing) frequency. By distancing the pulse frequency from the sources of mechanical vibrational noise which may be picked up by the PAS devices for measuring pressure variations, improvement in signal-to-noise ratios can be obtained.

Referring to the embodiment of FIG. 3, the photo-acoustic measurement system 200' may also include at least one optical filter 54 mounted between the electromagnetic source 48 and the optical window 52 for filtering the electromagnetic energy according to a range of wavelengths selected in relation to the specific target gas whose concentration is being measured in the sample gas in the resonant cavity 26. The optical filter 54 can be a band pass filter to narrow a range of radiation wavelengths entering the resonant cavity 26. The optical filter 54 is advantageously used to selectively excite components of the sample gas. It is to be appreciated that while in FIG. 3, the optical filter 54 has been shown as being a separate component, in alternative implementations the optical filter 54 may be incorporated into other components such as part of the optical window 52 and/or the optical chopper 64'.

For example, the optical window 52 may incorporate an optical filter for filtering the electromagnetic energy according to a range of wavelengths selected in relation to the specific target gas whose concentration is being measured in the sample gas in the resonant cavity 26.

The optical filter 54 may also be configured for allowing different specific wavelengths to be selectively generated in dependence of a selected specific target gas whose concentration is being measured in the sample gas in the resonant cavity 26. As an example, FIG. 7A shows an optical filter wheel 654 including a plurality of optical filters 54, wherein the plurality of optical filters includes optical filters associated to different wavelength to allow preferentially exciting different specific target gases. The optical wheel 654 may be operated with a filter wheel motor 505 as shown in FIG. 7A, so as to control which optical filter 54 to place between the electromagnetic source 151 and the at least one optical window.

While the FIG. 7A shows an optical filter wheel 654 containing a plurality of optical filters 54, it is to be appreciated that many other configurations, structures may be contemplated for generating signals of different wavelengths to allow preferentially exciting different specific target gases.

In an alternative example, not shown in the Figures, the optical filter wheel 654 may alternatively be replaced by one or more Fabry-Pérot interferometer assemblies for filtering the electromagnetic energy from the electromagnetic energy source. The one or more Fabry-Pérot interferometers may be configured to be adjustable such as to selectively filter frequencies within a frequency range. While the use of discrete optical filters, such as the type that may be used in an optical filter wheel 654, are inherently limited by the number of optical filter 54 to a corresponding number of specific individual frequency bands, Fabry-Pérot interferometer may be dynamically tuned along a continuum of frequencies within a frequency range in a more granular manner than would be allowed with discrete optical filters. As such, the use of this type of device for filtering the electromagnetic energy from the electromagnetic energy source may allow obtaining measurements for a more complete energy absorption spectrum and provide an improved ability to accurately quantify the concentrations of individual target gas species in a gas sample. This may be particularly advantageous in applications in which one or more of the target gas species have absorbing wavelengths which are close to the absorbing wavelengths of other gas species that may be present in the gas sample. Fabry-Pérot interferometers are known devices in the field of optics and will therefore not be described in further detail here.

Referring still to the embodiment of FIG. 3, the photoacoustic measurement system 200 may include a plurality of electromagnetic sources and with corresponding optical windows, such as for example two electromagnetic sources 48 48' and optical windows 52 52' as shown in this Figure. As shown in FIG. 3, the first and second electromagnetic sources 48 48' can be located at respective ends of U-shaped cavity. In certain applications, such configuration may be useful to detect and/or determine concentrations of two different specific target gases (e.g. a first specific target gas and second specific target gas) in a gas sample, for example by using the first electromagnetic source 48 for the first specific target gas, and using the second electromagnetic source 48' for the specific target second gas.

In certain embodiments, a single optical chopper 64', as shown in FIG. 3, may be used to provide pulsed electromagnetic energy 30 from the first electromagnetic and second electromagnetic sources 48 48'. In other embodiments (not shown in the Figures), each electromagnetic source 48 48' may be used with a corresponding optical chopper. In yet other embodiments, one single electromagnetic source 48 may be used for radiating towards both ends of the U-shaped cavity.

Decoupling Optical Chopper 64 from PAS Sound Measuring Device

As described above, certain embodiments of the photoacoustic spectroscopy (PAS) measurement system 200 include an optical chopper 64 operating in cooperation with the electromagnetic source 48 for producing pulsed radiations. Typically such optical chopper 64 has moving parts, for example a rotating wheel. When operating the optical chopper 64 at high frequencies, this type of chopper may create background noise in the form of vibrations and/or sound and/or air turbulence that may be picked up by the sound measuring device 66 (e.g., microphone) of the photoacoustic spectroscopy (PAS) measurement system 200. In such cases, this may render the photo-acoustic spectroscopy (PAS) measurement system 200 less sensitive in the detection of target gases. In particular, pressure variations due to air turbulence and/or enclosure vibrations caused by the operation of the chopper 64 can increase background noise and skew the acoustic readings of the analyser 20 and/or reduce its ability to detect small gas concentrations.

In order to improve the sensitivity of the of the analyser 20, at least some embodiments of the photo-acoustic spectroscopy (PAS) measurement system 200 include one or more damper elements for reducing vibrational interferences between the optical chopper 64 and the sound measuring device 66.

A first specific example of a damper element will now be discussed in the following section with reference to FIGS. 7A and 7C.

As shown in FIG. 7A, the PAS measurement system 200'''' may include an air turbulence damper element 500 for reducing pressure variations resulting from operating the optical chopper. The presence of such air turbulence damper element 500 decouples air pressure caused by the operation of the chopper 64 and operation of the sound measuring device 66. In other words, the air turbulence damper element 500 constitutes at least a partial air turbulence barrier that dampens changes in air pressure that, otherwise, may be picked up by the sound measuring device of the PAS measurement system as background noise.

Figure 7C:
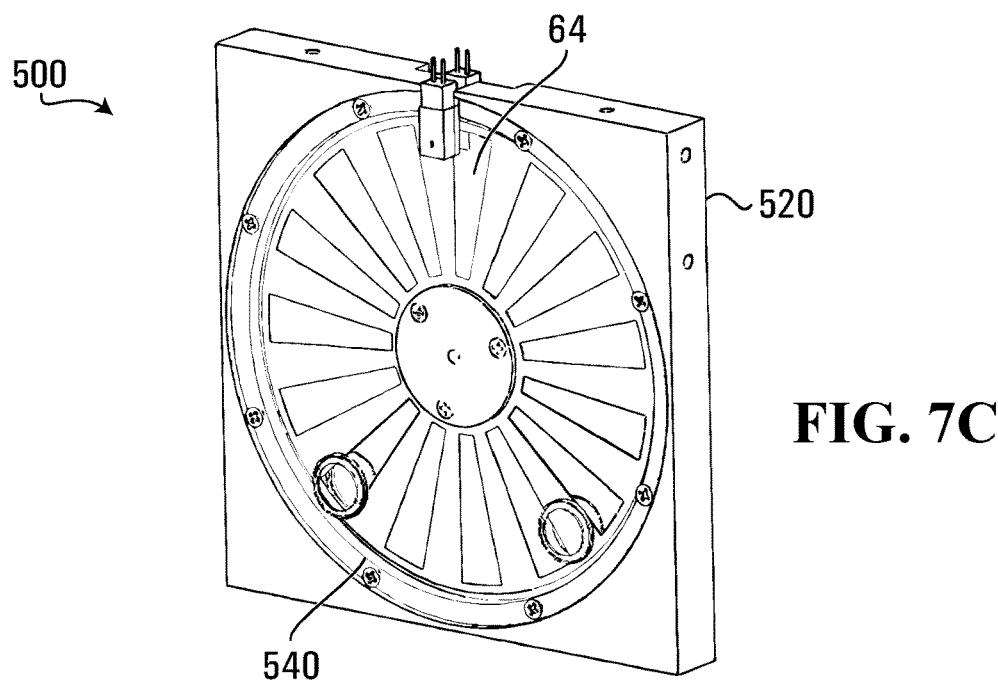
FIG. 7C shows a top isometric view of an optical chopper assembly for use in connection with the photo-acoustic spectroscopy (PAS) measurement system of FIG. 7A, in accordance with a non-limiting example of implementation of the present invention.

The air turbulence damper element 500 can best be seen in FIG. 7C. The air turbulence damper element 500 includes a chamber body 520 which defines a chamber 540 that at least partially encloses the optical chopper 64.

A second specific example of a damper element will now be discussed in the following section with reference to FIGS. 7A and 7D.

Figure 7D:
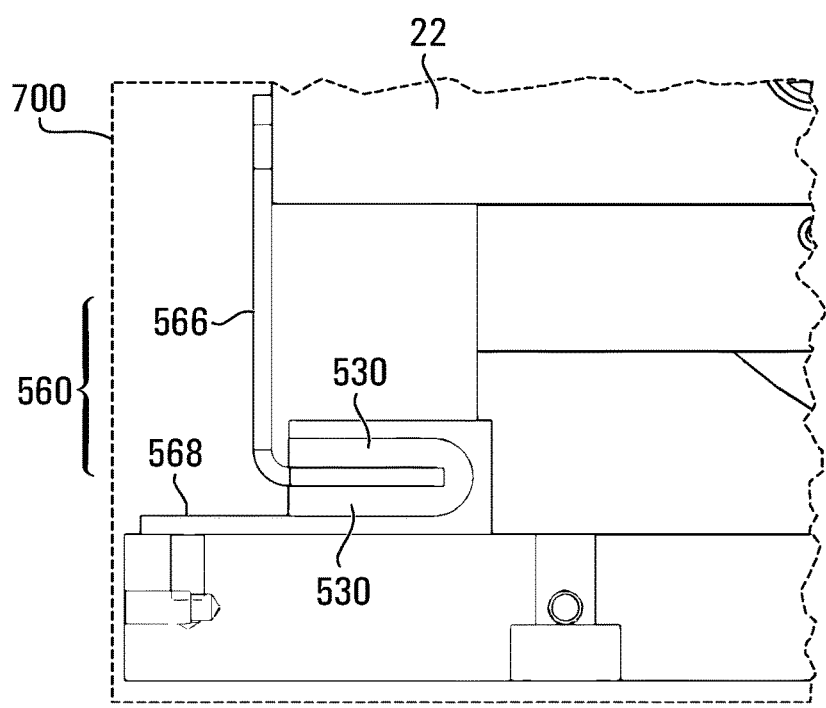
FIG. 7D shows a zoomed-in portion 700 of the photo-acoustic spectroscopy (PAS) measurement system of FIG. 7A showing a specific example of a manner of securing the photo-acoustic spectroscopy (PAS) measurement system body to a supporting structure located within the DGA apparatus 100 of FIG. 1, in accordance with a non-limiting example of implementation of the present invention.

FIG. 7D shows a zoomed view of a portion of the PAS measurement system 200 shown in FIG. 7A. The zoomed view insert 700 includes a compliant vibration damper element 530 for providing isolation between the optical chopper 64 and the sound measuring device 66 from vibrations resulting from operating the optical chopper 64. The presence of such vibration damper element 530 decouples vibrations caused by the operation of the chopper 64 from the sound measuring device 66. In other words, the vibration damper element 530 constitutes at least a partial barrier that dampens effects of vibrations that, otherwise, may be picked up by the sound measuring device of the PAS measurement system as background noise.

In the Figures (See FIGS. 7A, 7B, 7C and 7D), the measurement system 200'''' is shown as being mounted on a supporting structure 5, wherein the optical chopper 64 is mounted to the supporting structure 5 using supporting element 575 and the PAS body is mounted to the supporting structure 5 using supporting brackets 560.

The reader will recognize that the supporting brackets 560 can have a plurality of cooperating substructures or can have a single suitable structure form for allowing the PAS body to be mounted to the supporting structure 5. In the specific practical implementation shown in FIGS. 7A and 7D, cooperating mating structures are provided, namely a distal mounting section 568 secured to the supporting structure 5 and a proximal mounting section 566 secured to an external surface of the analyser body 22. The distal mounting section 568 is configured to receive the proximal mounting section 566 in an overlapping relationship to facilitate attachment of the two mounting sections together. In this specific example, the structural vibrational damper element 530 is shown as being located where both mounting sections 566, 568 matingly engage thereby allowing the vibration damper element 530 to minimize transmission of vibrations from the chopper 64 to the PAS body.

It will be understood that in some other specific example, the optical chopper 64 may be mounted to the supporting structure 5 using supporting brackets (not shown) where the vibration damper element 530 forms an interface between the supporting brackets and the supporting structure 5 to reduce a transfer of vibrations between the optical chopper 64 and the supporting structure, and ultimately, the sound measuring device 66.

Any suitable materials may be used in manufacturing the structural vibrational damper elements such as for example but without being limited to resilient foams, elastomers, springs and the like.

Gas Extraction Cell

As can be seen in the specific examples shown in FIGS. 1, 2, 3, 5 and 6, the gas extraction cell 76 includes a liquid inlet port 90 and a liquid outlet port 92 for connecting to the liquid circulation path 6 which transfers electrical insulating liquid from the electrical equipment 4 to the gas extraction cell 76, and from the latter into the former, in order to obtain sample of the electrical insulating liquid. The gas extraction cell 76 also includes fluid outlet port 190 and fluid inlet port 192 mounted thereon for connecting to fluid circulation path 8 which circulates a gas sample extracted from the sample of the electrical insulating liquid from the gas extraction cell 76 into the analyser 20, and from the latter into the former. It should be noted that the suggested locations of the ports 90, 92, 190 and 192 on the gas extraction cell 76 are just exemplifications and, therefore, other connectivity ports and other port locations connected to the gas extraction cell 76 can be considered.

The gas extraction cell 76 may be configured for extracting a gas sample from the sample of the electrical insulating liquid, including for example electrical insulating oil, using any suitable technique known in the art.

In some specific practical implementations, the gas extraction cell 76 may extract the gas sample from the sample of electrical insulating liquid using any suitable known head space extraction process. Briefly, headspace extraction is achieved by the diffusion of dissolved gases into the gas phase at constant temperature and pressure conditions until the equilibrium of coexistent phases is established. Optionally, elements for mechanically agitating the gas extraction cell 76 may be provided in the apparatus 100 for accelerating the extraction of gases from the electrical insulating liquid.

Figure 8:
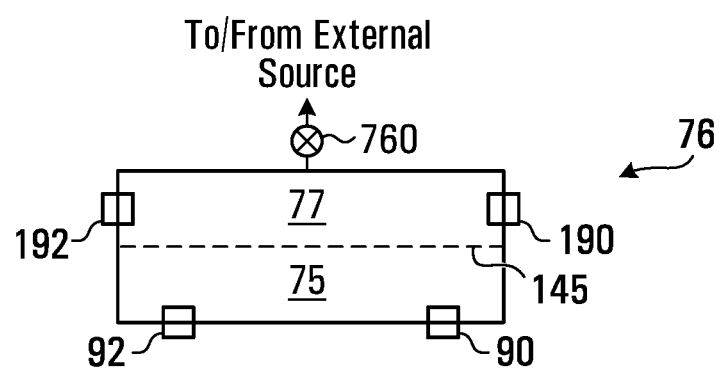
FIG. 8 shows a more detailed block diagram of the gas extraction cell 76 of the DGA apparatus 100 of FIG. 1 in accordance with a non-limiting example of implementation of the present invention.

In other specific practical implementations, the gas extraction cell 76 may extract the gas sample from the sample of the electrical insulating liquid using a semipermeable barrier 145 enclosed within the gas extraction cell 76, as illustrated in FIG. 8. The semipermeable barrier 145 is configured to preferentially permeate one or more components into the gas extraction space 77, such as gases and moisture from the electrical insulating liquid while simultaneously restraining the permeation of one or more other components, such as heavy hydrocarbon gases, electrical insulating liquid molecules, and droplets, into the gas extraction space 77. Advantageously, the use of such semipermeable wall 145 can help reduce or prevent exposure of optical components of the analyser 20 to damaging components present in the electrical insulating liquid, for example heavy hydrocarbons, thereby improving apparatus stability over time.

In one practical embodiment, the semipermeable barrier 145 may include a semi-permeable membrane which permeates gases but not transformer insulating liquids. Various geometries and physical constructions for the semipermeable barrier 145 will become apparent to the person of skill in the art in view of the present disclosure. Examples of such semi-permeable membranes are known in the art and, for the purpose of conciseness, will not be further described here.

Optionally, the gas extraction cell 76 and the PAS measurement system 200 may include a semi-permeable barrier between the channel 24 within the PAS measurement system 200 on one side and the extraction cell 76 on the opposing side thereof.

Other configurations useful for extracting dissolved gas from a liquid can be used in the apparatus 100 and will become apparent to the person of skill in the art in view of the present disclosure.

When extracting gas from a sample of electrical insulating liquid taken from a piece of electrical equipment, it has been observed that the total pressure of the extracted gas can vary significantly, e.g., from 1 to 16 pounds per square in absolute (PSIA), depending on the design, history and operational conditions of the piece of electrical equipment. Because the absorption response of each gas species in a gas mixture changes with total pressure of the mixture, the precision and accuracy of the PAS measurements may be affected by the pressure variations. Managing such gas pressure variability can, thus, have particular advantages in ensuring accuracy of the gas detection/quantification with the apparatus 100.

In order to account for and manage these pressure variations, a first approach may be to calibrate the pressure dependence the apparatus 100 so that pressure compensation may subsequently be applied to the measurements.

Another (second) approach to manage these pressure variations is to adjust the pressure in the extraction space 77 of the gas extraction cell 76 so that the total pressure of the gas sample lies within a narrower range. By setting that narrower pressure range to the pressure at which the apparatus 100 was calibrated and characterized, more precision and accuracy in the measurements of gas concentrations can be achieved.

In some specific practical implementations, the gas extraction cell 76 may be provided with a pressure regulating element 760 for mixing an external gas with the gas sample the extraction space 77 extracted from the sample of the electrical insulating liquid to obtain a mixed-gas sample such that the mixed-gas sample has a pressure approaching a target pressure. The pressure regulating element 760 may be in communication with an external reference gas source, such as for example a tank containing Nitrogen, or alternatively, the pressure regulating element 760 may be in communication with ambient air. While a specific location for one pressure regulating element 760 is shown in the figures, it will be apparent to the person of skill that other suitable locations and/or more than one pressure regulating element 760 may be present depending on specific applications.

In some specific embodiments, the target pressure may be, for example but not limited to, between 8 to 17 PSIA; preferable between 13 to 17 PSIA.

In some specific non-limiting embodiments, the target pressure may be near atmospheric pressure. It is to be appreciated that atmospheric pressure may vary in dependence of the altitude at which the apparatus 100 is installed. For example, the apparatus may be configured and calibrated to be installed at a specific geographical location and, as such, the target pressure would be near the atmospheric pressure at the specific geographical location.

As mentioned above, in some embodiments, the external gas mixed with the gas sample extracted from the sample of the electrical insulating liquid may be ambient air. In such embodiments, the pressure regulating element 760 may mix ambient air with the sample gas extracted from the liquid in such a manner that the total pressure of the gas sample is close to atmospheric pressure while the fault gas concentrations in the sample are close to equilibrium with the liquid. An advantage of using ambient air, in contrast to other possible gases, is that it is readily and freely available.

The pressure regulating element 760 may be an active pressure regulating element or alternatively may be a passive pressure regulating element.

In a specific practical implementation of an active pressure regulating element, the pressure regulating element 760 may include for example any suitable set of actionable valves and conduits known in the art for channeling an external gas into the gas extraction cell 76 until the gas extraction cell 76 approach the target pressure.

In a specific practical implementation of a passive pressure regulating element, the pressure regulating element 760 includes an elongated aperture comprised at least in part of capillary tubing. In specific practical implementations, the capillary tubing has a length and internal diameter configured to provide a restriction to the diffusion of specific target gas species, such that gas concentration gradients can be maintained across the ends of the capillary tubing while the pressure on either end of the capillary tubing is nearly equal. In some specific practical embodiments, the capillary tubing may have an internal diameter of about 0.01" (inches) and a length of about 8" (inches). It is however to be appreciated that other dimensions may also be used. For example, practical implementations with internal diameters between 0.005" and 0.02" have also been found to yield suitable results.

Dissolved Gas Analysis Process

The apparatus 100 is configured for performing dissolved gas analysis on the electrical equipment 4 having components immersed in electrical insulating liquid.

Figure 9:
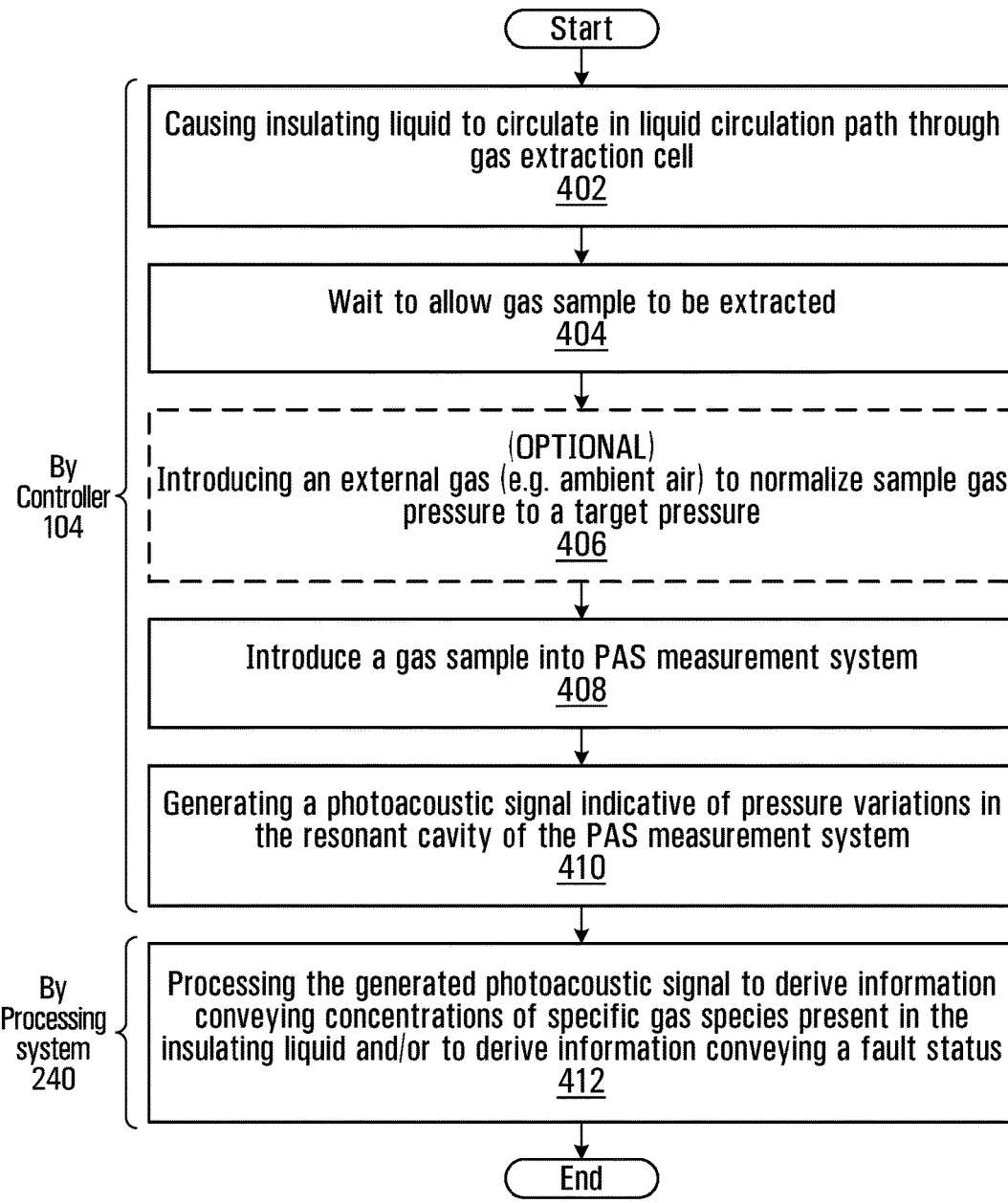
FIG. 9 is a flow diagram of a process implemented by the DGA apparatus 100 shown in FIG. 1 in accordance with a non-limiting example of implementation of the present invention.

A specific process that may be implemented by apparatus 100 is shown in FIG. 9.

With reference to FIG. 9, at step 402, electrical insulating liquid is caused to circulate through liquid circulation path 6 using pump 40 so that the insulating liquid goes through the gas extraction cell 76.

At step 404, the system waits for a certain time delay to elapse to allow a gas sample from the insulating liquid to be extracted by the gas extraction cell 77. Once the certain period of time has elapsed, the method then proceeds to optional step 406 or to step 408.

At optional step 406, using the pressure regulating element 760, an external gas is introduced into the gas sample extracted from the electrical insulating liquid to normalize the pressure so that the mixed-gas sample has a pressure approaching a target pressure. The method then proceeds to step 408.

At step 408, the gas sample is introduced into the photo-acoustic spectroscopy measurement system 200. The method then proceeds to step 410.

At step 410, the gas sample in the photo-acoustic spectroscopy measurement system 200 is excited using an electromagnetic energy source to produce a photo-acoustic signal associated with the gas sample. In some implementations, the electromagnetic energy source may produce a periodically pulsed beam of electromagnetic radiation with a chopping frequency greater than or equal to 150 Hz, for example a chopping frequency in a range between 150 Hz and 4000 Hz; preferably in a range between 200 Hz and 2000 Hz and most preferably still in a range between 500 Hz and 1000 Hz to limit interferences with noise sources in the lower frequency ranges.

It is to be understood that, while steps 402, 404, 406, 408 and 410 have been depicted in FIG. 9 as occurring sequentially, this was primarily done for the purpose of facilitating the understanding of the process and that one or more of steps 402, 404, 406, 408 and 410 may occur in an overlapping time sequence (e.g. simultaneously) and not necessarily sequentially.

At step 412, the photo-acoustic signal associated with the gas sample derived at step 410 is processed with the processing system 240 in order to derive information conveying concentrations of specific gas species present in the insulating liquid and/or to derive information conveying a fault status (or alternatively a fault level ranking) of the electrical equipment 4. Specific gas species whose concentration may be measured includes one or more of the following: carbon dioxide ($CO_2$), carbon monoxide (CO), ethane ($C_2H_6$), methane ($CH_4$), ethylene ($C_2H_4$), acetylene ($C_2H_2$), sulfur hexafluoride ($SF_6$) and any mixtures thereof. The concentrations of the dissolved gas species above may be reported in "parts per million" by volume (ppm) at a given temperature and pressure, commonly 0 degrees Celsius and 14.6 PSIA. For example, in a practical implementation, the processing system 240 may be configured to detect/quantify one or more of dissolved gas concentrations of at least 2 ppm CO (e.g., 2-50,000 ppm); at least 20 ppm $CO_2$ (e.g., 20-50,000 ppm); at least 2 ppm $CH_4$ (2-50,000 ppm); at least 0.5 ppm $C_2H_2$ (e.g., 0.5-50,000 ppm); at least 2 ppm $C_2H_6$ (e.g., 2-50,000 ppm); at least 2 ppm $C_2H_4$ (e.g., 2-50,000 ppm).

As shown in FIG. 9, in some implementations, steps 402 404 406 408 and 410 may be performed by the controller 104 and step 412 may be performed by the processing system 240.

Other practical examples of implementations will become apparent to the reader in view of the teachings of the present description and as such, will not be further described here.

Practical Example of Implementation for Processing System 240

Those skilled in the art should appreciate that in some non-limiting embodiments, all or part of the functionality previously described herein with respect to the processing system 240 of the apparatus 100 for providing the dissolved gas analysis functionality as described throughout this specification, may be implemented using pre-programmed hardware or firmware elements (e.g., microprocessors, FPGAs, application specific integrated circuits (ASICs), electrically erasable programmable read-only memories (EEPROMs), etc.), or other related components.

In other non-limiting embodiments, all or part of the functionality previously described herein with respect to the processing system 240 of the apparatus 100 may be implemented as software consisting of a series of program instructions for execution by one or more computing units. The series of program instructions can be tangibly stored on one or more tangible computer readable storage media, or the instructions can be tangibly stored remotely but transmittable to the one or more computing unit via a modem or other interface device (e.g., a communications adapter) connected to a computer network over a transmission medium. The transmission medium may be either a tangible medium (e.g., optical or analog communications lines) or a medium implemented using wireless techniques (e.g., microwave, infrared or other transmission schemes).

Those skilled in the art should further appreciate that the program instructions may be written in a number of suitable programming languages for use with many computer architectures or operating systems.

Figure 10:
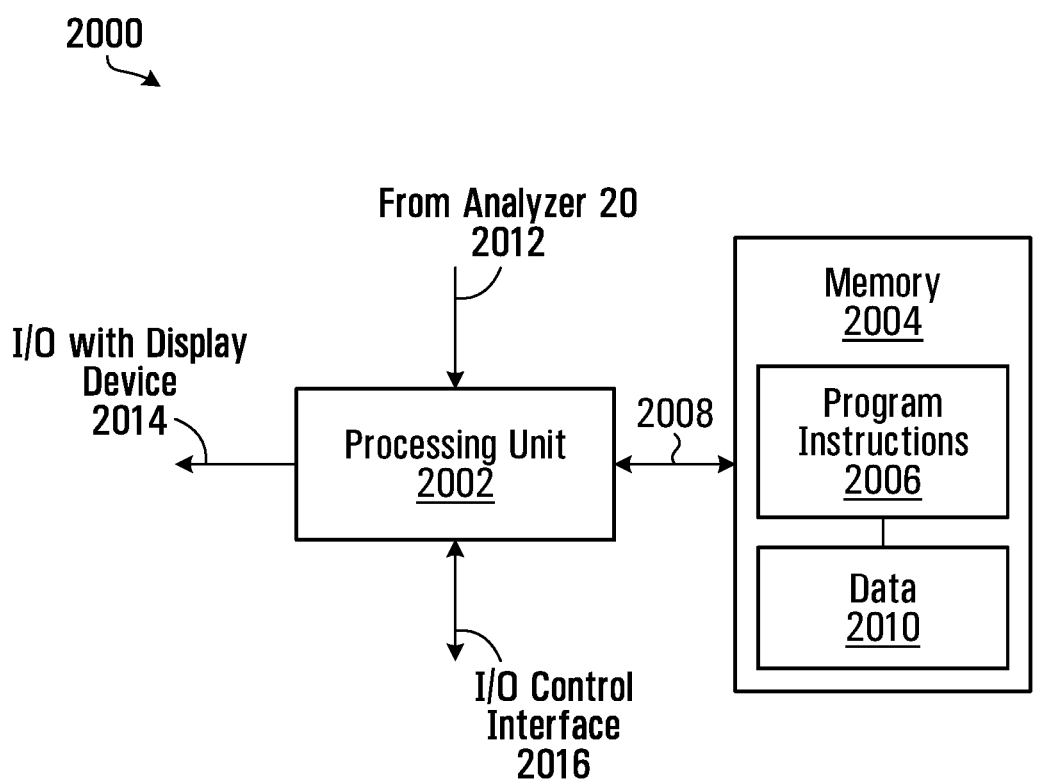
FIG. 10 is a block diagram of an apparatus suitable for implementing the processing system 240 of the DGA apparatus 100 of FIG. 1 in accordance with a specific example of implementation of the present invention.

In a non-limiting example, some or all the functionality of the processing system 240 may be implemented on a suitable microprocessor 2000, of the type depicted in FIG. 10. Such a microprocessor 2000 typically includes a processing unit 2002 and a memory 2004 that is connected by a communication bus 2008. The memory 2004 includes program instructions 2006 and data 2010. The processing unit 2002 is adapted to process the data 2010 and the program instructions 2006 in order to implement the functionality described and depicted in the drawings with reference to the processing system 240. The microprocessor 2000 may also comprise one or more I/O interfaces for receiving or sending data elements to external modules. In particular, the microprocessor 2000 may comprise an I/O interface 2012 with the analyzer 20 of the apparatus 100 (shown in FIG. 1), an I/O interface 2014 for exchanging signals with an output device (such as a display device) and an I/O interface 2016 for exchanging signals with a control interface (not shown).

General System for Providing DGA Monitoring and Analysis Functionality

The person skilled in the art will appreciate that, while the block diagram of the apparatus 100 depicted in FIG. 1 has shown some features for performing dissolved gas analysis on a piece of electrical equipment, it is to be appreciated that such features may constitute but a subset of the features within an actual commercial DGA apparatus.

Figure 11:
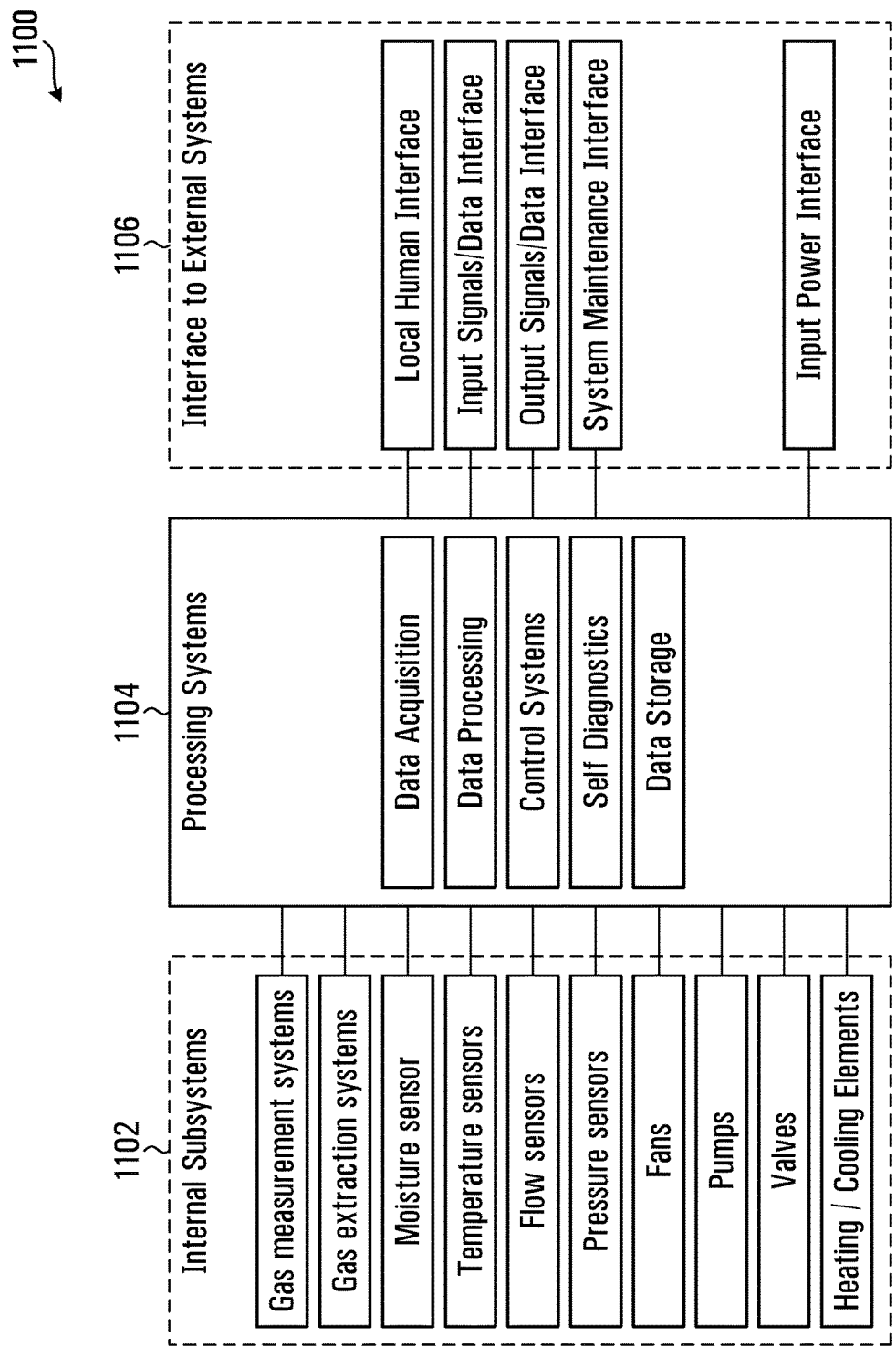
FIG. 11 is a block diagram showing three types of subsystems (internal 1102, processing systems 1104 and interfaces to external system 1106) interconnected to one another to provide DGA monitoring and analysis functionality, including functionality provided by the DGA apparatus depicted in FIG. 1, in accordance with a non-limiting example of implementation of the present invention.

FIG. 11 is a block diagram showing three types of subsystems (internal 1102, processing systems 1104 and interfaces to external system 1106) interconnected to provide DGA monitoring and analysis functionality. The subsystems may have many interconnections and data and control signals flow in both directions between many of them—these have been omitted for the purpose of clarity in the figure.

As depicted, internal subsystems 1102 may include, without being limited to, heating/cooling elements, flow sensors, temperature sensors, moisture sensors, other (complementary) gas measurement systems, other gas extraction systems, fans, pumps, valves, pressure sensors.

As depicted, the processing system 1104 may include, without being limited to, data acquisition, data processing (which may implement the functionality of processing unit 240 described above), control, self-diagnostics and data storage.

In addition, also as depicted, the interfaces to external systems 1106 may include, without being limited to, one or more local human interfaces, input signal/data interfaces, output signal/data interfaces, system maintenance interface and input power interfaces. The human interface may include any suitable display and/or illuminated indicators, and/or buttons and/or touch screen. Input signal/data interfaces may include interfaces for signals from external sensors (e.g. analogue inputs), and/or digital communications to effect the operation of the system. Output signal/data interfaces may include for example logic-level outputs (relays), analogue outputs and/or digital communications. The digital communications may be carried by copper, optical fiber, or wireless media, or any combination thereof. The digital communications may include, without being limited to, the use of Ethernet or Serial communication protocols, and may include the use of industrial communication protocols such as DNP3, Modbus, IEC 61850. The signals being sent/received through these interfaces (local human interfaces, input signal/data interfaces, output signal/data interfaces) may convey (for example but without being limited to) system status, system settings, measured concentrations and rates of change of concentrations of the dissolved gases and moisture in the insulating liquid, status of dissolved gas and/or moisture levels and rates of change in relation to pre-set thresholds, interpretations of dissolved gas and/or moisture levels based on algorithms adapted to that purpose, and system events. The system maintenance interface may include a digital communication interface to enable firmware updates and settings updates, for example. In addition, the input power interface may in some implementations be configured to monitor power quality, filter the incoming power, control conducted emissions, and protect the system from voltage spikes and power dropouts.

It will be appreciated by the person skilled in the art in view of the present description that the subsystems depicted in FIG. 11 have been shown for the purpose of illustration only and that a detailed description of these subsystems is beyond the scope of the present application and will thus not be described in further detail here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art in light of the present description that numerous modifications and variations can be made. The scope of the invention is defined more particularly in the appended claims.

What is claimed is:

1. An apparatus for performing dissolved gas analysis on a piece of electrical equipment having components immersed in electrical insulating liquid, the apparatus comprising:
   a. a liquid inlet and a liquid outlet connectable to the piece of electrical equipment for allowing electrical insulating liquid to circulate between the piece of electrical equipment and the apparatus through a liquid circulation path;
   b. a gas extraction cell in communication with the liquid circulation path, said gas extraction cell being configured for extracting a gas sample from the electrical insulating liquid;
   c. an analyser in fluid communication with said gas extraction cell for performing gas analysis on the extracted gas sample, said analyser including a photo-acoustic spectroscopy measurement system having an elongated channel including a resonant cavity and an electromagnetic energy source, wherein the resonant cavity includes a first portion and a second portion configured for containing at least part of the gas sample, wherein said first portion of the resonant cavity defines an optical pathway configured for propagation of electromagnetic energy from the electromagnetic energy source, and wherein the resonant cavity includes an element configured for obstructing the propagation of the electromagnetic energy from the electromagnetic energy source through the second portion of the resonant cavity, the photo-acoustic spectroscopy measurement system being configured to excite a portion of the gas sample contained in the optical pathway defined by the first portion of the resonant cavity to produce a photo-acoustic signal associated with the extracted gas sample;
   d. a processing unit programmed for deriving information associated with dissolved gas concentrations in the electrical insulating liquid at least in part by processing the photo-acoustic signal produced by the analyser.

2. An apparatus as defined in claim 1, wherein the element of the resonant cavity configured for obstructing the propagation of the electromagnetic energy includes an absorbing inner wall surface in a portion of the resonant cavity, said absorbing inner wall being configured for absorbing electromagnetic radiation.

3. An apparatus as defined in claim 1, wherein the element of the resonant cavity configured for obstructing the propagation of the electromagnetic energy includes a bend in the resonant cavity.

4. An apparatus as defined in claim 3, wherein the bend has a curvature configured for obstructing the propagation of the electromagnetic energy propagating through the resonant cavity.

5. An apparatus as defined in claim 1, wherein the resonant cavity is a U-shaped cavity.

6. An apparatus as defined in claim 1, wherein the resonant cavity includes a U-shaped cavity including two elongated portions and a curved portion linking the two elongated portions, wherein the first portion of the resonant cavity defining the optical pathway is one of the two elongated portions.

7. An apparatus as defined in claim 1, wherein the first portion of the resonant cavity has an inner wall including metallic deposits thereon.

8. An apparatus as defined in claim 7, wherein the metallic deposits include gold deposits.

9. An apparatus as defined in claim 1, wherein the resonant cavity has a substantially elongated tubular form.

10. An apparatus as defined in claim 9, wherein the resonant cavity has a substantially circular cross-section.

11. An apparatus as defined in claim 9, wherein the resonant cavity has an internal diameter which is substantially of constant size along the optical pathway.

12. An apparatus as defined in claim 9, wherein the resonant cavity has an internal diameter which is substantially of constant size along its extent.

13. An apparatus as defined in claim 9, wherein an internal diameter size of the second portion of the resonant cavity is no greater than an internal diameter size of the first portion of the resonant cavity defining the optical pathway.

14. An apparatus as defined in claim 9, wherein the first portion of the resonant cavity defining the optical pathway has a ratio of internal diameter size to optical pathway length in a range between 0.2 and 0.01.

15. An apparatus as defined in claim 1, wherein the gas extraction cell includes a semi-permeable membrane for extracting the gas sample from the electrical insulating oil.

16. An apparatus as defined in claim 1, wherein the gas sample that said gas extraction cell is configured for extracting from the electrical insulating liquid has a volume of less than 10 cubic centimeters.

17. An apparatus as defined in claim 1, wherein the gas sample that said gas extraction cell is configured for extracting from the electrical insulating liquid has a volume between 3cc and 10cc.

18. An apparatus as defined in claim 1, wherein the information associated with the dissolved gas concentrations in the insulating liquid derived by the processing unit conveys concentrations of one or more specific gases selected from the group consisting of carbon dioxide ($CO_2$), carbon monoxide (CO), ethane ($C_2H_6$), methane ($CH_4$), ethylene ($C_2H_4$), acetylene ($C_2H_2$), sulfur hexafluoride ($SF_6$) and any mixtures thereof.

19. An apparatus as defined in claim 1, wherein said photo-acoustic spectroscopy measurement system includes a plurality of optical filters associated with respective frequency bands corresponding to particular target gases.

20. An apparatus as defined in claim 19, wherein said photo-acoustic spectroscopy measurement system includes an optical wheel assembly including at least some of the plurality of optical filters.

21. An apparatus as defined in claim 1, wherein said photo-acoustic spectroscopy measurement system includes one or more Fabry-Pérot interferometer assemblies for filtering the electromagnetic energy from the electromagnetic energy source.

22. An apparatus as defined in claim 1, wherein said apparatus is configured for establishing a communication link over a computer network with a remote computing device for transmitting the derived information associated with dissolved gas concentrations in the electrical insulating liquid.

23. An apparatus as defined in claim 22, wherein the remote computing device is a smartphone.

24. An apparatus as defined in claim 1, wherein said apparatus comprises a pump for circulating the electrical insulating liquid through the liquid circulation path.

25. An apparatus as defined in claim 1, wherein said piece of electrical equipment includes at least one of a transformer, a tap-changer and a circuit breaker.

* * * * *